United States Patent [19]

Quistad et al.

[11] Patent Number: 5,554,592
[45] Date of Patent: Sep. 10, 1996

[54] INSECTICIDAL TOXINS FROM THE PARASTIC WASP, BRACON HEBETOR

[75] Inventors: Gary B. Quistad, Mountain View, Calif.; Douglas J. Leisy, Corvalis, Oreg.

[73] Assignee: Sandoz Ltd.

[21] Appl. No.: 288,408

[22] Filed: Aug. 10, 1994

Related U.S. Application Data

[63] Continuation of Ser. No. 13,890, Feb. 5, 1993, abandoned, which is a continuation-in-part of Ser. No. 897,192, Jun. 10, 1992, abandoned, which is a continuation-in-part of Ser. No. 847,570, Mar. 4, 1992, abandoned.

[51] Int. Cl.$^6$ .................... A61K 38/16; C07K 14/435; A01N 27/00; A01N 63/00
[52] U.S. Cl. .................... 514/12; 530/350; 530/858; 424/538
[58] Field of Search .................... 424/405, 538; 514/2, 12; 530/350, 858; 930/210; 435/69.1

[56] References Cited

PUBLICATIONS

Slavnova et al. 1987. "Effect of Toxins from the venom of the Ichneumon *Habrobracton hebetor* (SAY) . . ." *Doklady Akademii Nauk SSR* 297(2):492–494.

Visser et al. 1983. "Characterization of Two Paralysing Protein Toxins (A–MTX and B–MTS) . . ." *Comp. Biochem. Physiol.* 75B(3):523–530.

Piek et al. 1982. "The Pharmacology of *Microbracon* Venom" *Comp. Biochem. Physiol.* 72C:303–309.

Spanjer et al. 1977. "Two Different Paralysing Preparations Obtained from a Homogenate of the Wasp *Microbracon hebetor*" *Toxicon* 15:413–421.

Visser et al. 1976. "Isolation and Some Biochemical Properties of a Paralysing Toxin from the Venom . . ." *Toxicon* 14:357–370.

Walther et al. 1983. "Block of Synaptic Vesicle Exocytosisi Without Block of $Ca^{2+}$ Influx . . ." *Neuroscience* 9(1):213–224.

Drenth 1974. "Susceptibility of Different Species of Insects to an Extract of the Venom Gland of the Wasp Microbracon hebetor" (SAY) *Toxicon* 12:189–192.

Beard 1971. "Production and Use of Venom by Bracon brevicornis (WESM)" in *Toxins of Animal and Plant Origin* vol. 1 deVries et al., Eds. Gordon and Breach Science Publishers, New York, pp. 181–190.

Piet 1966 "Site of Action of Venom of *Microbracon hebetor* SAY (Braconidae, Hymenoptera)" *J. Insect Physiol.* 12:561–568.

*Primary Examiner*—Dian C. Jacobson
*Attorney, Agent, or Firm*—Lynn Marcus-Wyner

[57] ABSTRACT

Novel polypeptides are isolated from the venom of the parasitic wasp, *Bracon hebetor*, and are designated Brh-I to Brh-V. These polypeptides are paralytic and/or toxic to insects. The entire amino acid sequence of Brh-I and the DNA encoding it is also determined. These polypeptides may be cloned into a baculovirus, and used for insect control.

6 Claims, 7 Drawing Sheets

5,554,592

INSECTICIDAL TOXINS FROM THE PARASTIC WASP, BRACON HEBETOR

This is a continuation of application Ser. No. 08/013,890, filed Feb. 5, 1993, now abandoned, which is a continuation-in-part of application Ser. No. 07/897,192, filed Jun. 10, 1992, now abandoned, which is a continuation-in-part of application Ser. No. 07/847,570, filed Mar. 4, 1992, now abandoned.

This invention is directed to toxins active against insects which are isolated from the parasitic wasp *Bracon hebetor*, the nucleic acids which encode the toxins, cloning of the toxins, use of the toxins to control insects, and genetically engineered virus vectors carrying the toxin gene.

BACKGROUND OF THE INVENTION

In recent years, venoms of insects and arachnids, in particular spiders and scorpions, have been investigated as a potential source of biologically active substances for use in various fields such as medicine and agriculture. Examples of such work include:

EP Patent Application, Publ. No. 208 523 A2: Glutamate Antagonists Isolated from New World Spiders *Argiope trifasciata* and *Araneus gemma*.

EP Patent Application, Publ No. 156 540: Glutamate Receptor Inhibitor obtained from *Nephila clavata*.

Grishin et al., 1986. "Ion Channel Blocker from the Venom of *Argiope lobata*" *Biorg. Khim.* 12(8): 1121–1124.

Usherwood et al., 1984. "Glutamate Channel Blockade by Venoms of *Argiope trifasciata* and *Araneus gemma*" *J. Physiol. Paris* 79: 241–245.

Aramaki et al. 1986. "Glutamate Potential Suppressor from *Nephila clavata* and *Nephila maculata*" *Proc. Japan Acad.* 62, Ser B: 359–362.

Usherwood et al., 1985. "Antagonism of Glutamate Receptor Channel Complexes by Spider Venom Polypeptides" *Neurotoxicology* 6(2): 239–250.

Adams et al. 1986. "Synaptic Toxins from *Agelenopsis aptera*" *Insect Neurophysiology*, Borkovec et al., Eds. Humana Press, Clifton, N.J. 397–408.

*Bracon hebetor* (also known as *Habrobracon hebetor* and *Microbracon hebetor*) is a small (ca. 2 mm, less than 1 mg) ectoparasitic wasp, which has a venom that is paralytic to lepidopterans (Drenth, D. 1974, *Toxicon* 12: 189–192). The quest to identify toxins in *B. hebetor* venom has continued for several years (see, e.g. Visser et al, 1976, *Toxicon* 14: 357–307; Visser et al, 1983, *Comp. Biochem. Physiol.* 75B: 523–530; and Spanjer et al, 1977, *Toxicon* 15: 413–421). Most attempts have been frustrated by the lability of the toxins. Two protein toxins (mol. wt. 44 and 57 kda) have been purified and partially characterized, but they represent only 2% of the original insecticidal activity (Visser et al, supra, 1983). More recently, Slavnova et al, 1987 *Doklady Akademii Nauk USSR* 297: 492–494 reports isolation of a toxin having a mass of 18 kda.

DESCRIPTION OF THE INVENTION

It has now been found that certain polypeptides, when isolated from the venom of the wasp *Bracon hebetor* are toxic, i.e. paralytic and/or lethal to insects, particularly of the order Lepidoptera, at surprisingly low concentrations.

The present invention, therefore, concerns toxins free from associated wasp polypeptides which demonstrate toxicity towards insects. These polypeptides may be isolated from, or be constructed to show substantial sequence homology to polypeptides isolated from the venom of *Bracon hebetor*. Preferred peptides are rather large, and may be characterized in having a molecular weight which exceeds 70,000 da. Five preferred polypeptides were isolated and were designated Brh-I to Brh-V.

As used throughout the specification and claims, the following definitions are intended:

Associated wasp polypeptides—polypeptides naturally occurring in the venom of *B. hebetor* which are toxic to insects.

Homologous polypeptide—a polypeptide which is identical to one of the native toxins of this invention, or substantially homologous (at least 80%) with respect to the amino acid sequence, such that it demonstrates substantially the same insect toxicity in in vivo assays as a native toxin.

Homologous nucleotide sequence—a sequence which will hybridize to the reference sequence under stringent hybridization conditions.

Stringent hybridization conditions—those in which hybridization is effected in a standard manner at 65° C. in 4× buffered saline (a.k.a. SSPE buffer) followed by merely washing at 52° C. in 0.2× SSPE, which will not affect true hybrids which have formed.

Figure 1:
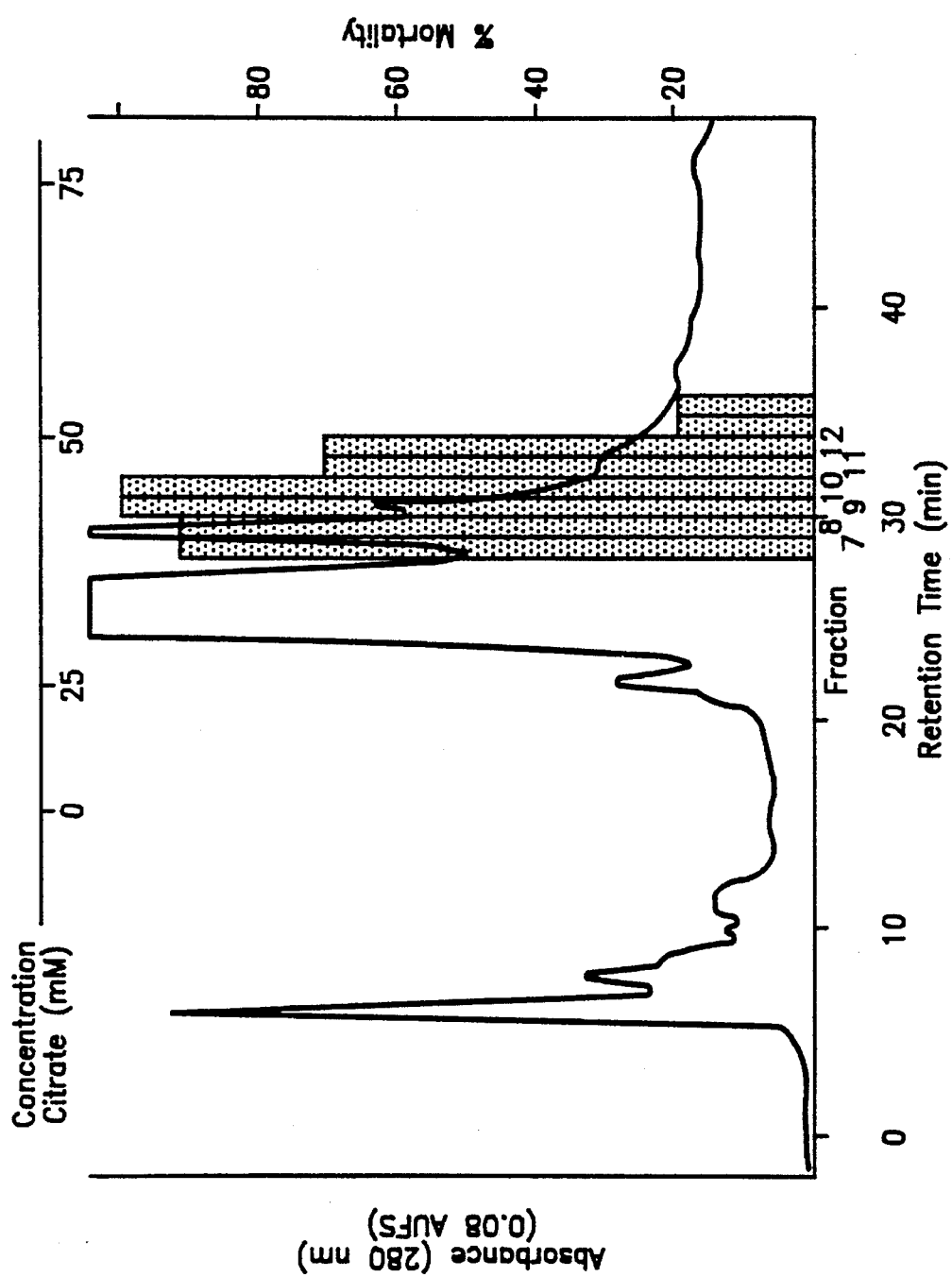
FIG. 1 demonstrates the purification of toxins from 300 *B. hebetor* venom glands using anion-exchange chromatography.

The toxins of this invention are quite labile under many isolation conditions. As they are particularly unstable at low pH, reverse-phase HPLC was contraindicated. The successful structure elucidation of toxins which are part of this invention is predicated on the purification by anion-exchange chromatography which was monitored by reversed-phase HPLC. The results of the anion-exchange chromatography are shown in FIG. 1. Various fractions, designated Fractions 7–13 are identified, and their insect mortality is assessed.

Figure 2:
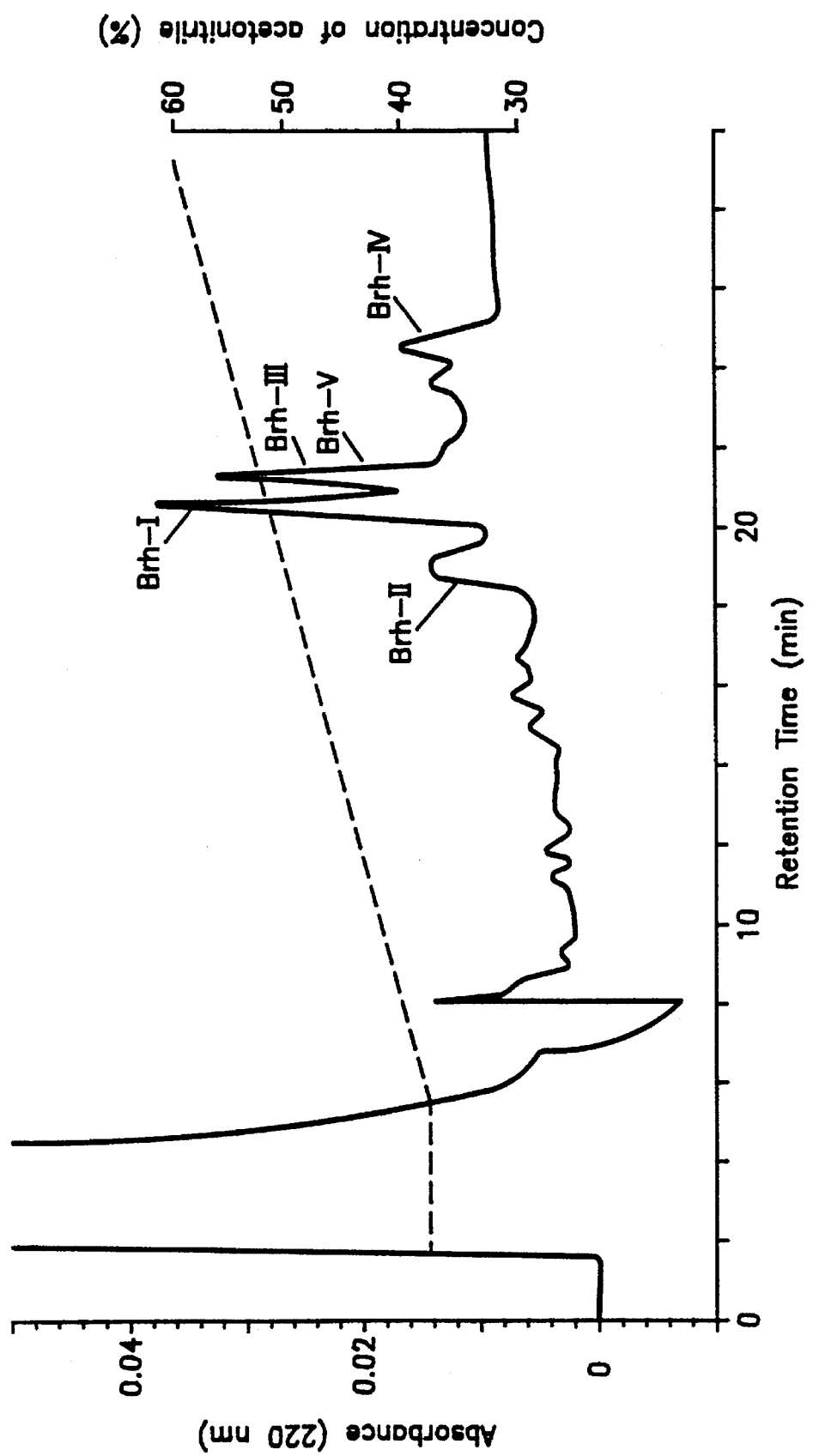
FIG. 2 is the reversed-phase HPLC analysis of combined fractions 7–13 from FIG. 1, using 25 gland-equivalents.
Figure 3:
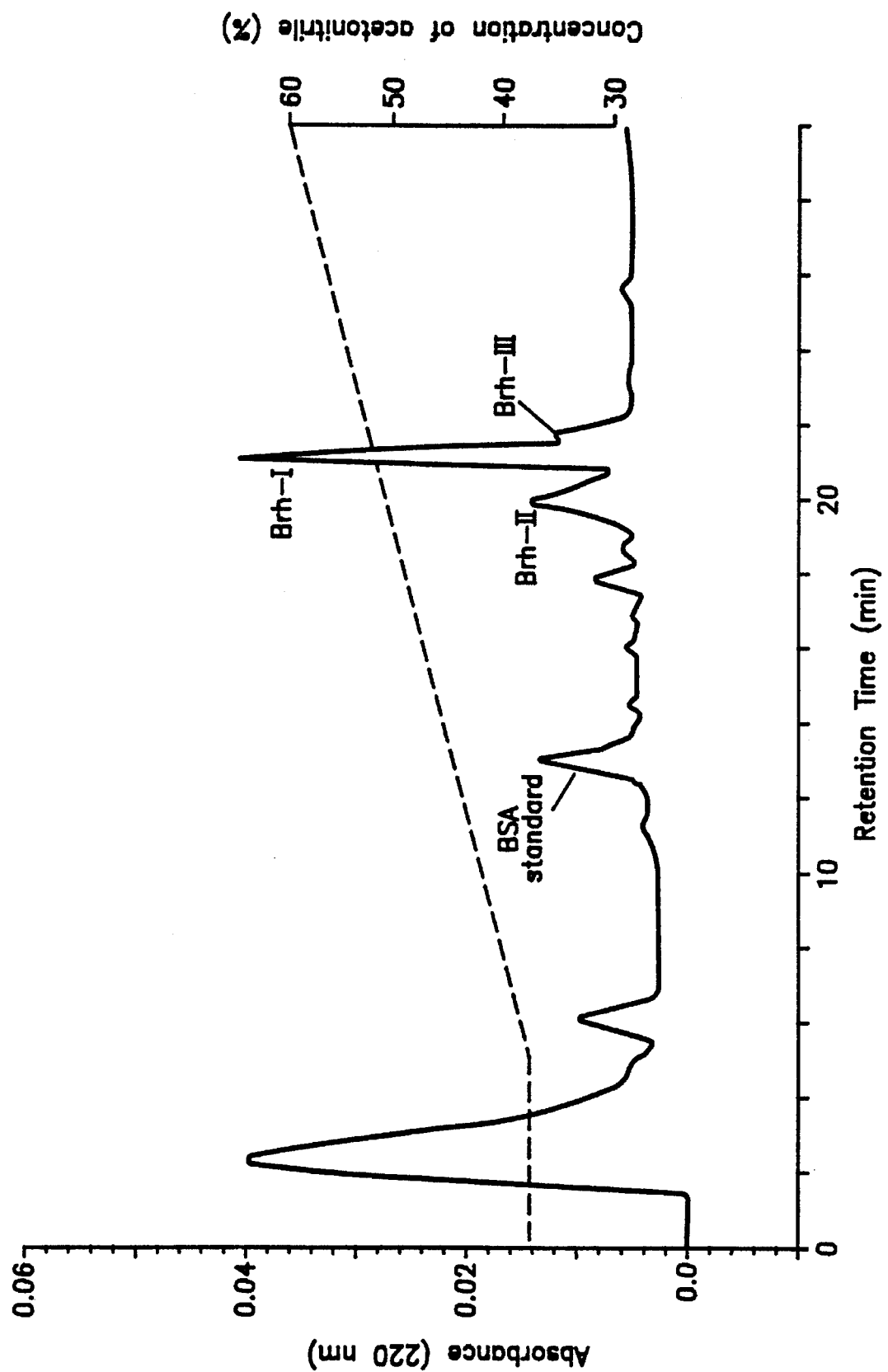
FIG. 3 is the reversed-phase HPLC analysis of Fraction 8 from FIG. 1 (25 gland equivalents). This is predominantly Brh-I.
Figure 4:
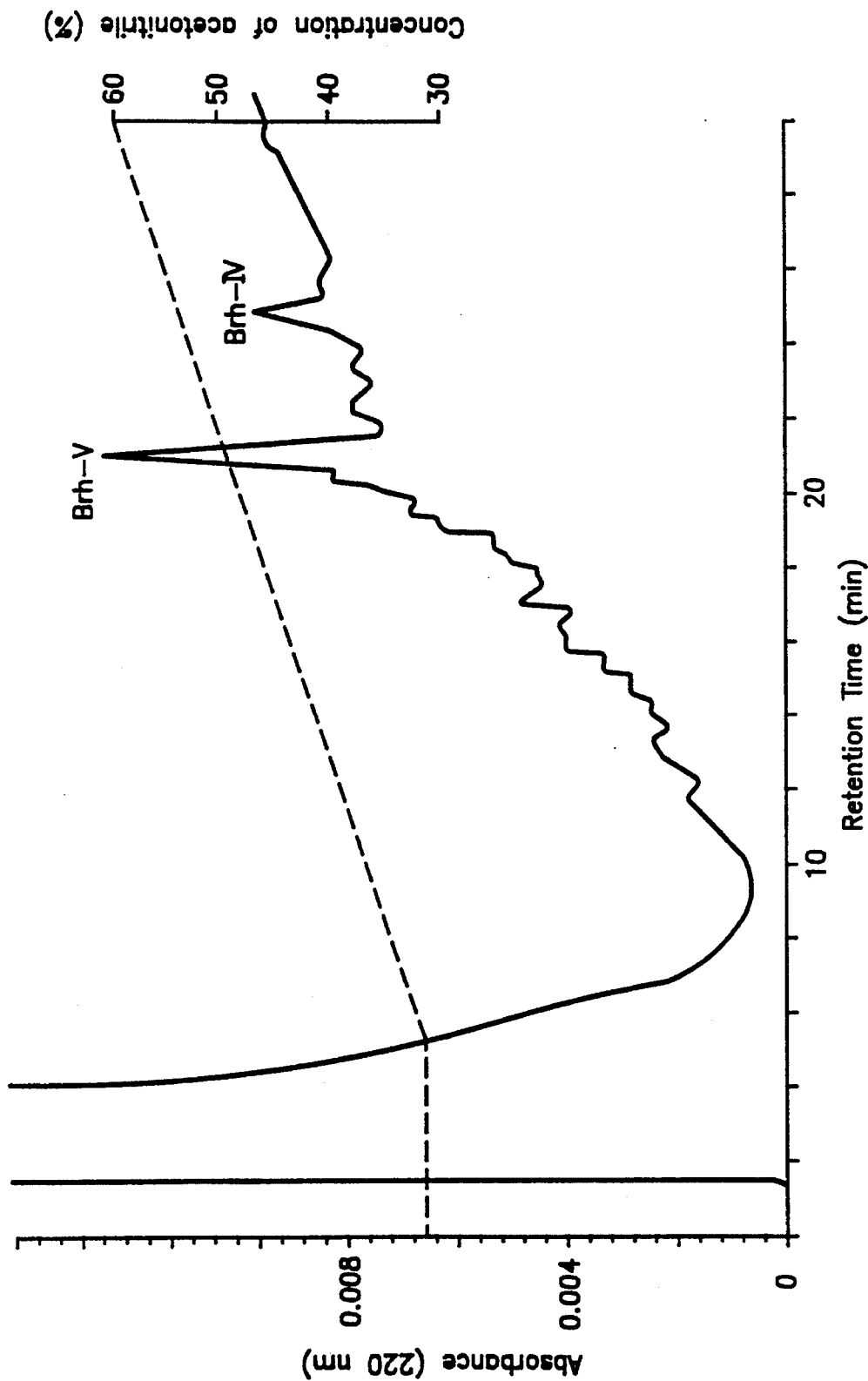
FIG. 4 is the reversed-phase HPLC analysis of Fraction 11 from FIG. 1 (25 gland equivalents). This is predominantly Brh-V.

As ultraviolet absorbance was of limited utility during toxin purification by ion-exchange, short (1 min) fractions were collected relative to contaminant absorbance (280 nm) and each fraction was assayed for bioactivity and purity (typically 25 gland equivalents using reverse-phase HPLC). Results are illustrated in FIGS. 2, 3, and 4.

In order to consistently recover toxins exhibiting high bioactivity, it was necessary to add a protein carrier (bovine serum albumin) prior to desalting by membrane filtration.

Purified toxins could not be freeze-dried, even in the presence of BSA and were best stored in a solution (0.02 M ammonium carbonate, pH 9.2, 4° C.). Under these conditions, the toxins were stable for at least two weeks.

Thus one aspect of this invention is a polypeptide free from associated wasp polypeptides substantially homologous to a polypeptide isolated from *Bracon hebetor* and exhibiting insect toxicity. Preferred polypeptides have a molecular weight of at least 70,000 da. Examples of prefered polypeptides of this invention include: Brh-I, Brh-II, Brh-III, Brh-IV and Brh-V.

The preferred polypeptides of this invention may be characterized by their behavior during Anion-Exchange and Reversed-Phase HPLC as follows, the complete conditions of which are given in Example 1. By following the procedures set forth in Example 1, ie. Anion-Exchange chromatography followed by Reversed-Phase chromatography, peaks characteristic of Brh-I, Brh-II, Brh-III, Brh-IV, and Brh-V can be identified.

Three of the five native toxins were sequenced at least partially. Results are presented below.

TABLE 1

```
         1       5      10         15        20       25
Brh-I    T D F   Y Y T D V I  A D Q D F L L K Q K K V F Q L
Brh-II   H V Q   T Y T A D M D F K H K Q K K I Y H L F ——
Brh-III  L F D   F I V H A K D I L G G I D N L A K G I —I/Q
                        30       35        40
Brh-I    L Y H V  S Q P —I S N ——————F Q ——L K  (SEQ. ID. NO.: 1)
Brh-V    — —   Q                                (SEQ. ID. NO.: 2)
Brh-III  A I N K  V ——V I —K V Q —Q A            (SEQ. ID. NO.: 3)
```

The polypeptides of this invention may be prepared by a variety of techniques. They may, for example, be isolated from the crude venom of *B. hebetor* using purification techniques, such as those presented in the Examples. Alternatively, with knowledge of the amino acid sequence of the polypeptides, synthetic construction, using conventional protein synthesis techniques may be employed.

A further technique which may advantageously employed in the production of polypeptides of this invention involves the construction, by conventional methods, of a DNA sequence which, upon expression, encodes a polypeptide according to this invention. Such DNA sequences may then be inserted into an appropriate vector, either alone or in combination with other homologous or heterologous DNA sequences whose function may be to control the expression of the polypeptide-encoding DNA sequence of interest or may result in, for example, a fusion protein, enhancing or extending the activity of the toxin DNA expression product therefrom. Suitably employed as vectors are plasmids, phages, and viruses, the use of which for such purpose is common knowledge to the ordinary artisan. Cells in which a vector containing such a toxin DNA may be expressed, include, for example, prokaryotic cells such as *E. coli*, and Bacillus spp., or eukaryotic cells such as yeast cells or insect cells.

A preferred method for producing the toxin polypeptides directly as a toxic product such that no work-up towards isolation, purification, and formulation of an expression product is required is by employing an insect specific virus (baculovirus) as a vector. A gene encoding the desired polypeptide toxin is inserted into the baculovirus DNA, and is under the control of a baculovirus promoter. After the recombinant hybrid baculovirus is ingested by the insect, the virus multiplies inside the insect and the toxin is expressed (produced) in an amount sufficient to enhance the virus' insecticidal effect on the insect. Such a recombinantly modified baculovirus DNA may also be used as a vector for the introduction of the wasp toxin-producing gene into cells, particularly insect cells, to provide further systems for the production of toxins.

A number of baculoviruses are suitable for use as vectors, and are known in the art, such as the nuclear polyhedrosis virus from *Autographa californica, Heliothis virescens,* and *Bombyx mori.* Suitable techniques are described, for example in European Patent Application 0175 852 and U.S. Pat. No. 4,745,051, both of which are hereby incorporated by reference.

Thus, other aspects of this invention are nucleic acids sequences (RNAs and DNAs) comprising those which encode toxin polypeptides and nucleic acid sequences which are substantially homologous to a native sequence. The nucleic acid sequences of this invention may also include sequences which are not expressed in the final polypeptide product, such as signal sequences, termination sequences, and the like.

A further aspect of this invention, therefore involves the cloning and genetic engineering of genes encoding the various toxins, and in particular Brh-I. While Brh-I is presented as an Example, any of the polypeptides of this invention may be similarly sequenced and cloned.

Starting with approximately 3.1 g of wasps, approximately 8 µg of poly A+ mRNA was obtained using the procedures detailed in the Examples. Degenerate oligonucleotide primers corresponding to two regions of the nucleotide sequence obtained by reverse translation of the mature Brh-I peptide were synthesized and used for PCR amplification from *B. hebetor* mRNA. DNA fragments with the expected size of approximately 130 bp were produced in the PCR reaction. The DNA fragments were gel purified, cloned into pTZ18R, and three clones were sequenced. All three of these clones contained a reading frame that matched a portion of the amino acid sequence of mature Brh-I toxin. A nondegenerate primer designed to match a region from within the amplified sequence was end-labelled with $^{32}$P and used to screen a λZAPII cDNA library made from *B.hebetor.* Three positive plaques were detected in a library screening of approximately $1.2 \times 10^6$ plaques.

After plaque purification and in vivo excision of the cDNA containing pBluescript SK– plasmids from the λZAPII clones, the cDNA inserts of 3 clones were subjected to DNA sequence analysis. In order to determine the expected size of a full length cDNA, a primer extension reaction was performed with *B. hebetor* mRNA. The nucleic acid and amino acid sequence of Brh-I is given in TABLE 2 (SEQ. ID. NO.: 4 and SEQ. ID. NO.: 5). Translational initiation very likely occurs at the ATG as indicated in TABLE 2 because a) this is the first methionine codon encountered in the cDNA; b) the codon for methionine is found in the sequence ATAATGC, which conforms with the ribosome initiation site consensus sequence determined by Kozak, M., 1989, *J. Cell Biol.* 108: 229–241; and c) there is a translational stop sequence, TAA, in frame with the Brh-I open reading frame just upstream from this methionine codon. The predicted translation product for the cDNA is a molecule of 678 amino acids. The amino acid sequence given in TABLE 2 has an 18 amino acid sequence at the N-terminus preceding the sequence determined by analysis of the isolated polypeptide (Table 1). As this 18 amino acid sequence has many of the properties expected for a signal sequence (see, e.g., von Heijne, G. *Nucl. Acids Res.* 14: 4683–4690) it appears that this sequence is a signal sequence which is cleaved after translation.

The molecular weight of mature Brh-I predicted from the cDNA sequence is 77,912. This is somewhat larger than the value determined by SDS-PAGE analysis of isolated Brh-I (approximately 73,000), however, the amino acid composition determined for Brh-I and for the cDNA translation product agree within experimental error, suggesting that no other extensive proteolytic processing occurs besides signal sequence cleavage.

Because of the very high level of paralytic activity that Brh-I elicits upon injection of a number of different insects, cDNAs encoding Brh-I toxin may be cloned in an insect baculovirus. Upon expression in the insect, there will be a quicker cessation of feeding than occurs after infection with wild type baculoviruses. Insect baculoviruses occur in two forms, occluded viruses, which are responsible for the spread of viruses between insects, and nonoccluded or budded viruses which are responsible for the cell to cell spread of viruses within an infected insect. Infection of insects per os normally requires the occluded form of the virus. Thus a further aspect of this invention is a recombinant virus containing a gene encoding a toxin of this invention inserted at a locus such that occlusion body formation is not disrupted. One such locus is the p10 locus.

Polypeptides isolated from or those showing substantial homology to those isolated from the venom of *B. hebetor* are useful as insect toxic agents. In particular, they are useful toxic agents against insects of the order Lepidoptera, for example, *Heliothis virescens, Autographa californica,* and the insects of the genus Spodoptera. Both the purified toxin and viruses transformed to produce the toxin are assayed for bioactivity on larvae including: tobacco hornworms (*Manduca sexta*), tobacco budworms (*Hellothis virescens*) and beet arrmyworm (*Spodoptera exigua*). Toxicity is demonstrated by the ability of the polypeptides to cause paralysis and/or death of the test larvae.

The present invention also provides the use of polypeptides isolated from, or polypeptides showing substantial sequence homology to those isolated from *Bracon hebetor* as insect toxic agents. For use as insecticides, the recombinant viruses which produce polypeptides of the invention may be combined with suitable carrier substances such as those typically found in insect control formulations, such as adjuvants, diluents, modifiers or conditioning agents. The formulations may be in the form of solutions, emulsions, dispersions, powders, dusts, granules and the like. It may be advantageous to include a surface active agent such as DMSO in the formulation so that the toxin passes directly through the cuticle of the insect and avoids the digestive enzymes which might affect its activity.

These compositions are advantageously applied to the insect or its locale in an amount suitable to control the target insects. By control, as used herein, is meant the induction of paralysis, mortality, or cessation of eating. Dosages of the composition of the invention will depend on numerous factors, including the pest to be controlled and the climatic conditions, but will generally be in the range of 0.5 to 100 kg/hectare, preferably 10–50 kg/hectare.

The following non-limiting Examples are presented to better illustrate the invention.

EXAMPLE 1

Isolation of Toxins

*B. hebetor* adult wasps are purchased from Biofac, Inc., Mathis Tex. Upon arrival, wasps are frozen at −20° C. until used. Venom glands and associated tissue are removed from female wasps and are stored in 1.5 ml polypropylene tubes at −20° C. until processed.

Purification. Lots of 100 venom glands are homogenized manually with a glass pestle in 1 ml water. After centrifugation at 3000× g, the supernatants from 300 glands are passed through Bio-Rad 10 DG size-exclusion columns. The excluded fraction (mol. wt >6 kda) is purified by ion-exchange chromatography.

Anion-exchange chromatography is performed with a Perkin-Elmer pump (410 BIO), a Spectra-Physics ultraviolet detector (Model 8300, 280 nm) and an Altex column (Spherogel-TSK, DEAE-SPW, 7.5×75 mm) with a elution at 1 ml/min. The elution solvent is citrate in 0.02M ammonium carbonate containing 10% aceto-nitrile, pH 8.2:0 mM titrate for 15 min, linear gradient to 25 mM over 5 min, and 25 to 75 mM over 50 min. Individual fractions are bioassayed using *M. sexta* larvae. As shown in FIG. 1, all insecticidal activity is found in one broad zone (Fractions 7–13). Collectively, these fractions contain several wasp toxins (See FIG. 2, 3 and 4), but only 59 µg total protein from 300 venom glands, representing an approximately 4000-fold purification of toxins based on initial whole wasp mass.

Reverse phase liquid chromatography (HPLC) is performed using a Hewett Packard (HP) pump (Model 1090), an HP diode array detector (Model 1040, 220 and 280 nm), and a narrow-bore Vydac $C_4$-300 A column (15×0.2 cm) with a flow rate of 0.3 ml/min. The eluent is acetonitrile in 0.1% trifluoroacetic acid: 35% for 5 min, linear gradient 35 to 60% over 25 min. HPLC demonstrates that most individual fractions from ion-exchange chromatography are mixtures of toxins. However, fractions 8 and 11 are sufficiently pure to allow further characterizations. Fraction 8 contains predominantly Brh-I while Fraction 11 contains mostly Brh-V (See FIGS. 3 and 4).

Figure 5:
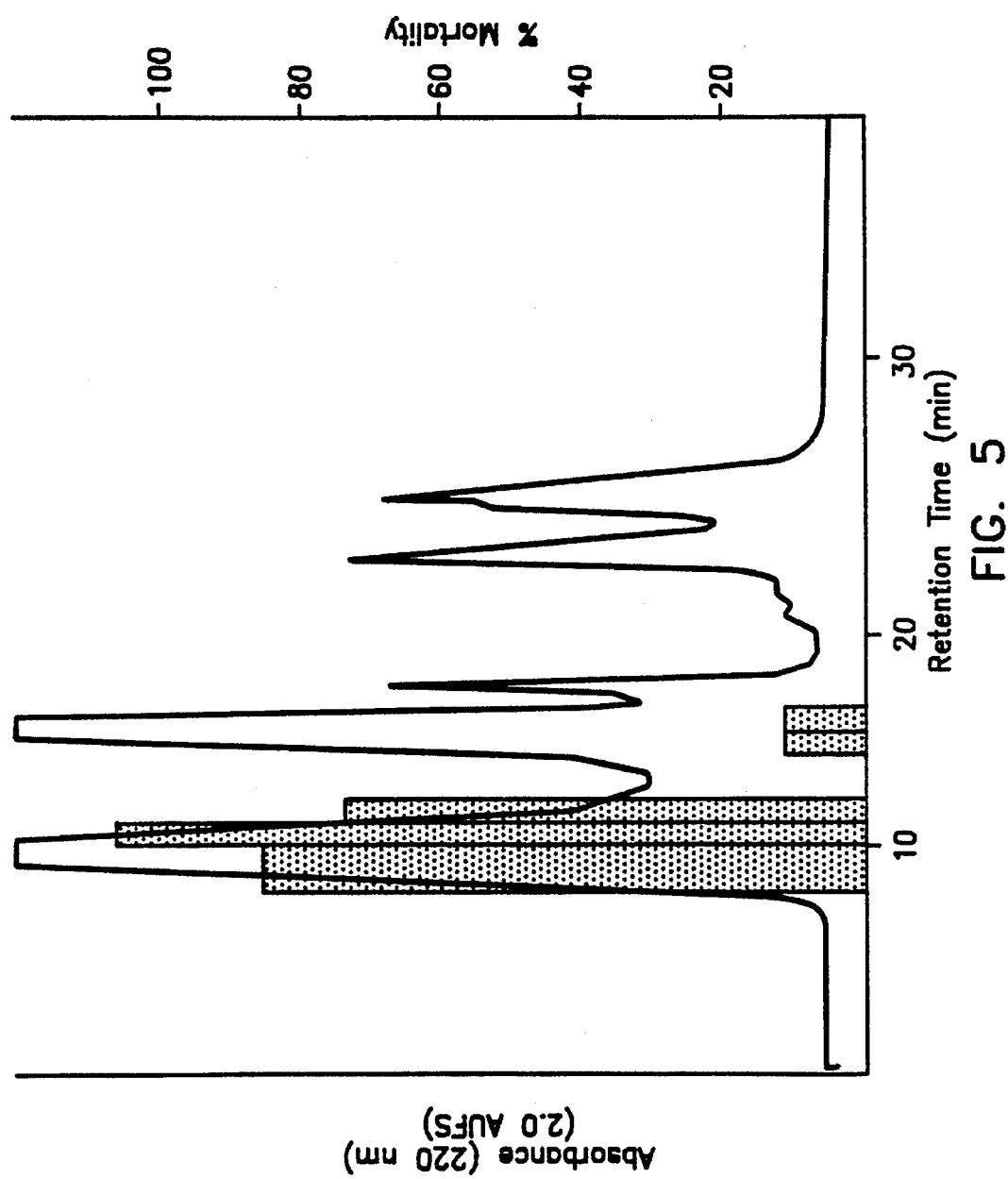
FIG. 5 is the size-exclusion HPLC analysis of toxins from 80 *B. hebetor* venom glands.

Size-exclusion chromatography employed the same Perkin-Elmer pump and Spectra-Physics detector as above with an Altex Spherogel-TSK 3000SW column (7.5×300 mm) with a flow of 0.5 ml/min. The eluent is 10% acetonitrile. Results are shown in FIG. 5.

EXAMPLE 2

Bioassay

The bioactivity of whole venom glands is determined for 50 glands homogenized in ice water. After centrifugation at 3000× g, 3 µl aliquots are injected into the pronotum of lepidopteran larvae which are scored for mortality at 24 hrs. The lethal dose for 50% of the treated larvae ($LD_{50}$) is calculated by Probit analysis from duplicate lots of glands, each of with at least four dose rates.

Purified Brh-I and Brh-V toxins are assayed similarly. Prior to the bioassay, 1 min. fraction from the ion-exchange purification are desalted using CentriconU\U-10 microconcentrators (Amicon). Bovine serum albumin (100 μg) is added to samples prior to desalting to improve recovery of toxins. Toxins are concentrated to approximately 150 μl in 0.02M ammonium carbonate for bioassay.

The following larvae are bioassayed: *Manduca sexta* (tobacco hornworm) third stadium; *Heliothis virescens* (tobacco budworm) fourth stadium; *Helicoverpa zea* (corn earworm) fourth stadium; *Spodoptera exigua* (beet armyworm) fifth stadium; *Galleria mellonella* (wax moth) fourth stadium; *Trichoplusia ni* (cabbage looper) fifth stadium; *Pieris rapae* (cabbage butterfly) third stadium; and *Diabrotica undecimpunctata* (western spotted cucumber beetle) third stadium. Results are presented in Tables 3 and 4, below.

TABLE 3

Bioactivity of Venom Gland Extract

| | mass of larva (mg) | $LD_{50}$ glands/larva | $LD_{50}$ glands/g |
|---|---|---|---|
| M. sexta | 47 | 0.036 | 0.77 |
| H. virescens | 48 | 0.080 | 1.7 |
| S. exigua | 50 | 0.065 | 1.3 |
| G. mellonella | 61 | 0.00046 | 0.0076 |
| H. zea | 41 | 0.038 | 0.95 |
| T. ni | 66 | 0.0014 | 0.021 |
| D. undecimpunctata | 13 | >0.2 | >13 |
| P. rapae | 56 | 0.000073 | 0.0013 |

TABLE 4

| | Injection Assay | |
|---|---|---|
| | $LD_{50}$ (μg/g) Brh-I | $LD_{50}$ (μg/g) Brh-V |
| M. sexta | 0.05* | 0.04* |
| S. exigua | 0.033* | 0.051* |
| H. virescens | 0.18* | 0.26* |
| H. zea | 0.045* | 0.085 |
| G. mellonella | 0.0023* | 0.00011 |
| T. ni | 0.019 | 0.0038 |

*Duplicate toxin isolation for bioassay

EXAMPLE 3

Sequence Analysis 900 venom glands are processed as described above. Purified toxins (43–77 pmol) are sequenced twice using an Applied Biosystems Model 477A pulsed liquid phase protein sequencer. Released phenylthiohydantoin amino acids are analyzed using an on-line analyzer (Applied Biosystems Model 120A). Brh-I is also converted to a reduced, carboxymethylated derivative prior to sequencing as described in Skinner et al, 1989 *J. Biol. Chem.* 264: 2150–2155, which is hereby incorporated by reference.

Toxins Brh-I and Brh-V are analyzed for constituent amino acids after hydrolysis in vacuo by vapor from 6M HCl/1% phenol at 110° C. for 20 hrs. Hydrolysates are analyzed using a Hewlett Packard AminoQuant amino acid analyzer.

EXAMPLE 4

Isolation of mRNA

*B. hebetor* wasps are stored at −80° C. 3.15 g of both male and female wasps are homogenized with a Polytron for 1 min in 20 ml RNA extraction buffer (4M guanidine isothiocyanate, 50 mM sodium citrate, pH 7.0, and 0.1M 2-mercaptoethanol). Following homogenization, 1 ml 15% Sarkosyl is added. The homogenate is centrifuged at 8,000 rpm for 10 min at 4° C. in a Sorvall HB-4 rotor, and the supernatants are decanted into clean tubes to remove insoluble debris. This is repeated once and the supernatant is layered over 3 ml of 5.7M CsCl in 0.01M EDTA, pH 8.0, and is centrifuged for 17 hours at 35,000 rpm in a Beckman Ti55 rotor. The pellet is resuspended in 15 ml of FastTrack Lysis Buffer (Invitrogen Corp) and the mRNA is then isolated following the protocol provided by Invitrogen Corp for their FastTrack mRNA isolation kit.

EXAMPLE 5

PCR Amplification

Single-stranded cDNA is synthesized from *B. hebetor* mRNA (0.5 μg) using M-MLV reverse transcriptase (GIBCO-Bethesda Research Laboratories) primed with a degenerate 20-mer oligonucleotide primer with the following sequence (SEQ. ID. NO.: 6)

5'-A[A,G][C,T]TG [A,G]AA[ACGT]AC[C,T]TT[C,T]TT[C,T]TG-3'

This primer is complementary to a sequence derived by reverse translation of the Brh-I toxin N-terminal amino acid sequence. Following the cDNA synthesis, the reactions are heated to 90° C. for 5 minutes, cooled to room temperature and ethanol precipitated. The cDNA reaction product is amplified in a 50 μl reaction with PCR geneAMP reagents (Perkin-Elmer Cetus Instruments), using 2 μM each of the above primer and a second degenerative primer with the following sequence (SEQ. ID. NO.: 7):

5'-GA [C,T]TT[C,T]TA[C,T]TA[C,T]AC[A,C,G,T]GA[C,T]GT-3'

This primer corresponds to a second portion of the reverse translation product of the Brh-I toxin N-terminal amino acid sequence. PCR conditions are as follows: 1 min at 94° C.; 2 min at 37° C.; slow ramping of the temperature over 3 min to 72° C.; 3 min at 72° C.; 10 sec extension of the 72° C. segment per cycle for 30 cycles; and a final cycle extension of 72° C. segment for 10 min. The products of the PCR reaction are electrophoresed on a 2% Agarose gel in TBE buffer (Sambrook et al, 1989 *Molecular Cloning: A Laboratory Manual, 2nd Ed.* Cold Spring Harbor Laboratory Press, Cold Spring Harbor, N.Y.). A gel slice expected to contain the approximately 70 bp product is removed, and the DNA is isolated using Geneclean (Bio101) reagents according to the manufacturer's instructions. The DNA is then reamplified using the same primers and the same PCR conditions as described above.

The DNA fragments are then gel-purified and cloned into pTZ18R (BIORAD Laboratories) and three clones are sequenced. All three clones match the Brh-I sequence from Table 1. A non-degenerate primer, designed to match a region from within the amplified sequence (See Table 5) is end-labeled with $^{32}$P and used to screen a λZAPII cDNA library made from *B. hebetor* mRNA. Three positive plaques are detected in a library screening of approximately 1.2×10⁶ plaques. One of the Brh-I positive clones has an insert size of approximately 3.0 kb, and the other two each have inserts of approximately 2.3 kb.

TABLE 5

Reverse translation and PCR Amplification of Brh-I toxin mRNA. The amino acid sequence of amino acids 2 through 32 from the N-terminus of Brh-1 toxin is shown on line 1. The nucleotide sequence derived by reverse translation of the Brh-I amino acid sequence is shown below the amino acid sequence on line 2. All possible nucleotides at each position are indicated Y = C or T; R = A or G; M = A or C; W = A or T; H = A, C, or T; N = A, C, T, or G. Degenerate oligonucleotides corresponding to the first underlined region and the complement of the second underlined region are used as PCR primers for amplification from Brh-I mRNA. Lines 3, 4, and 5 show the nucleotide sequence from three cloned PCR fragments. Underlined sequences correspond to primer regions. Line 6 shows the sequence of the nondegenerate oligonucleotide which was used as a hybridization probe for screening the *B. hebetor* cDNA library.

```
                       5                            10                          15
1       Thr Asp Phe Tyr Tyr Thr Asp Val Ile Ala Asp Gln Asp Phe Leu Leu Lys
Gln 2   ACN GAY TTY TAY TAY ACN GAY GTN ATH GCN GAY CAR GAY TTY YTN YTN AAR

CAR
 3          GAT TTT TAT TAT ACT GAT GTG ATA GCT GAT CAA GAT TTC CTT TTA AAG

CAA
 4          GAC TTT TAT TAC ACT GAC GTG ATA GCT GAT CAA GAT TTC CTT TTA AAG

CAA
 5          GAT TTT TAT TAT ACT GAT GTG ATA GCT GAT CAA GAT TTC CTT TTA AAG

CAA
     6                                              3'-CAC TAT CGA CTA GTT CTA AAG G-5'
                                                                          (SEQ. ID. NO.: 8)

20                       25                      30
1       Lys Lys Val Phe Gln Leu Leu Tyr His Val Ser Gln Pro    (SEQ. ID. NO.: 9)
2       AAR AAR GTN TTY CAR YTN YTN TAY CAY GTN WSN CAR CCN    (SEQ. ID. NO.: 10)

3       AAG AAG GTT TTT CAA TT                                 (SEQ. ID. NO.: 11)

4       AAA AAG GTA TTT CAA CT                                 (SEQ. ID. NO.: 12)

5       AAG AAG GTA TTT CAA CT                                 (SEQ. ID. NO.: 13)
```

DNA sequencing and Sequence Analysis. Double stranded pBluescript SK-plasmid DNA containing cDNA inserts are generated from λZAPII cDNA clones following the in vivo excision procedure described in the λZAPII instruction manual. The 5'-termini of the cDNA inserts are then subjected to PCR amplification using the primer indicated in Table 5 coupled with M13 reverse primer. The PCR products from the 5'-termini of the 2.3 kb cDNA inserts have identical sequences and that from the 3.0 kb cDNA sequence is the same as those of the 2.3 kb cDNA except for being shorter by four nucleotides.

The two XhoI fragments from within the cDNA insert are subcloned into the pBluescriptSK+II vector, and unidirectional deletion series are generated from both ends of each clone. Both strands of the cDNA are sequenced in their entirety, and is given in Table 2 (SEQ. ID. NO. 4 and SEQ. ID. NO.: 5).

The nucleotide sequences and predicted protein sequences are analyzed with the IntelliGenetics suite of sequence analysis programs.

EXAMPLE 5

Construction of Vectors

Figure 6:
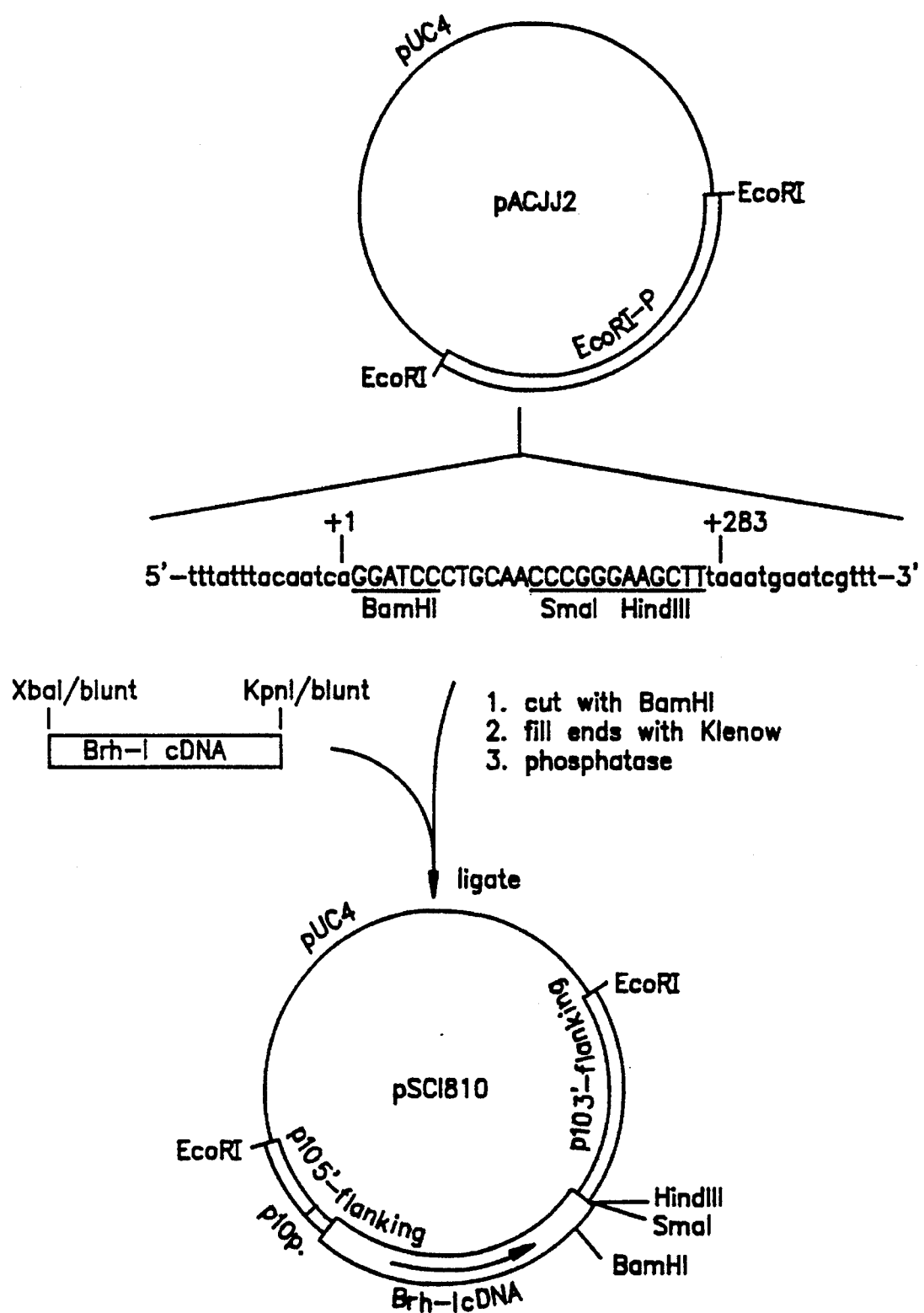
FIG. 6 is a diagram of plasmid pSCI810, containing the Brh-I gene.

A plasmid containing the Brh-I cDNA is liberated from a recombinant λZAPII isolate by in vivo excision. The plasmid is cut with XbaI and KpnI, treated with Klenow in the presence of all four dNPTs to make the ends blunt, and then the cDNA containing insert is gel isolated. The plasmid pACJJ2, (obtained from Dr. Just Vlak, Dept. of Virology, Agricultural Univ., Wageningen, The Netherlands) which has a polylinker in place of the complete p10 open reading frame, is cut with BamHI, the ends are filled, phosphatased with calf intestinal phosphatase, and then is ligated with the isolated Brh-I cDNA to form pSCI810, as shown in FIG. 6.

Next, pBluescript KS⁺ and pBluescript SK⁺ are each digested with KpnI and XholI, treated with Klenow in the presence of dNPT's to make the ends flush, and then religated to form pBluescript KS⁺ΔXK and pBluescript SK⁺ΔXK, respectively. Each of these plasmids is then digested with ScaI and SalI. The larger of the two fragments from the ScaI and SalI digested pBluescript KS⁺ΔXK and the smaller of the two fragments from the ScaI and SalI digested pBluescript SK⁺ΔXK are isolated and ligated together to form pSCI235. Another plasmid, pSCI839 is constructed by subcloning an approximately 3 kb SalI fragment containing an intact polyhedrin gene into pSCI234 to form pSCI839. The SalI fragment containing the polyhedrin gene in pSCI839 is isolated from pSCI275, which is a pWE15-based cosmid vector containing a large segment of AcNPV DNA (randomly cloned from AcNPV strain LI) that includes the polyhedrin gene.

Figure 7:
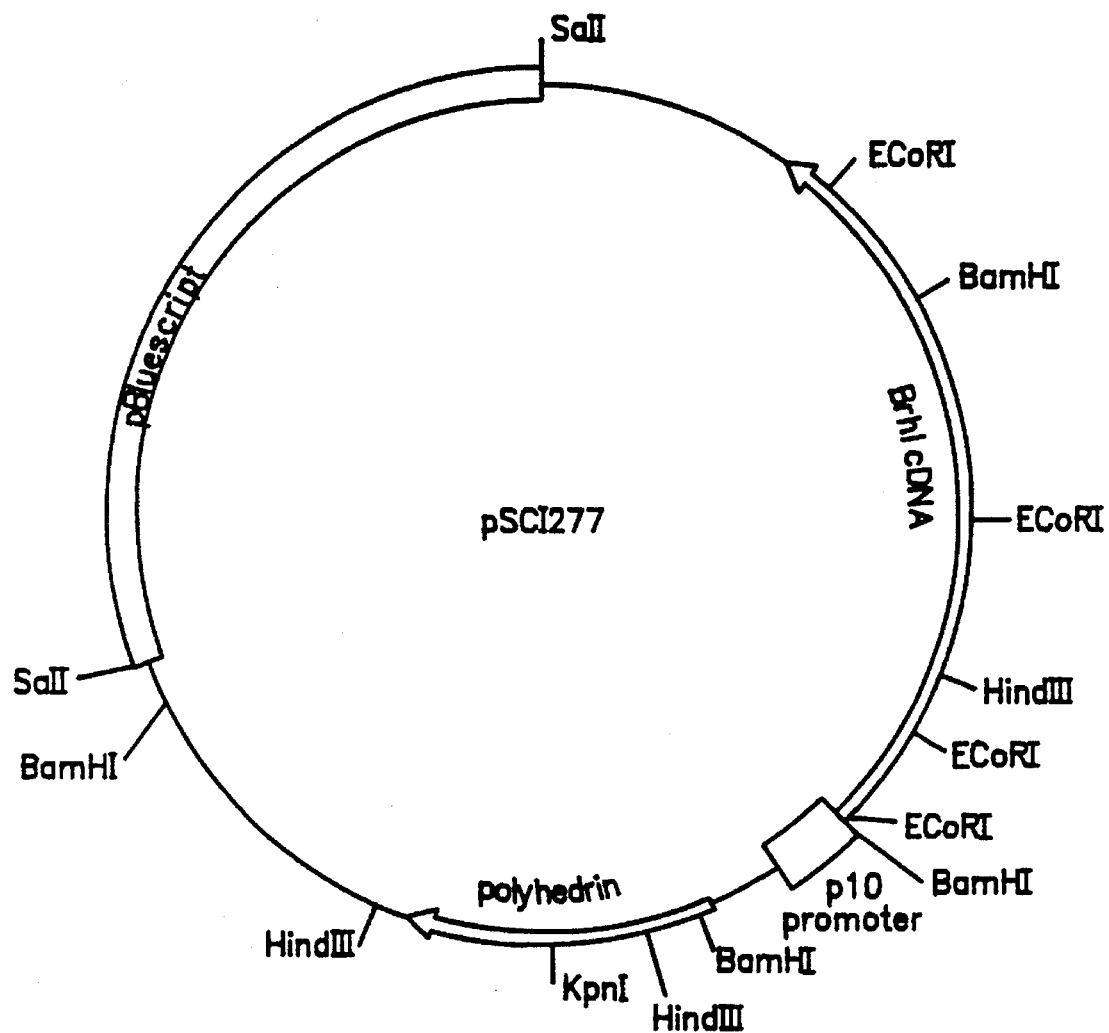
FIG. 7 is a diagram of plasmid pSCI277, containing the Brh-I gene linked to the p10 promoter.

Plasmid pSCI276 is formed by cutting pSCI810 with PstI and SpeI, making the ends blunt with T₄ DNA polymerase in the presence of dNTPs, and is religated. pSCI276 is then cut with SphI and SmaI, the SphI ends are made flush with T₄ DNA polymerase in the presence of dNTPs, and an approximately 2650 bp segment containing the Brh-I cDNA linked to the p10 promoter is isolated and cloned into the unique EcoRV site of pSCI839 to form pSCI277. The plasmid pSCI277 has a module containing the p10 promoter region linked to the Brh-I cDNA inserted at the EcoRV site just upstream of the intact polyhedrin gene; it is diagrammed in FIG. 7. After transfection of this plasmid with polyhedrin⁻ viral plasmid DNA, recombinant viruses are selected by their ability to form polyhedra⁺ plaques.

TABLE 2

BRH-I (SEQ. ID. NOS. 4 & 5)

```
GCAACACAAG TGTTACTTCG TTTGCCACTT CACTGTTGAA GAAAAATAAA AAATACATTT         60

TGATTATCAC TTGAATAATC TATA ATG CTG AAG AAG GTC TTT CTT TTG GCC          111
                            Met Leu Lys Lys Val Phe Leu Leu Ala
                             1                5

TCT TTG GCT ATT ATC GTG ATA AAA GCT GAT ACC GAT TTT TAT TAT ACA         159
Ser Leu Ala Ile Ile Val Ile Lys Ala Asp Thr Asp Phe Tyr Tyr Thr
 10               15                  20                     25

GAT GTG ATA GCT GAT CAA GAT TTC CTT TTA AAG CAA AAG AAA GTT TTT         207
Asp Val Ile Ala Asp Gln Asp Phe Leu Leu Lys Gln Lys Lys Val Phe
                 30                  35                  40

CAA TTG TTG TAT CAT GTT TCA CAA CCA GAC ATC TCA AAT CCC GAG CTT         255
Gln Leu Leu Tyr His Val Ser Gln Pro Asp Ile Ser Asn Pro Glu Leu
             45                  50                  55

TTC CAG GAG GGA TTG GCT TAT GAC ATT GGA GCC AAT ATT GAT TCC TAT         303
Phe Gln Glu Gly Leu Ala Tyr Asp Ile Gly Ala Asn Ile Asp Ser Tyr
             60                  65                  70

TCT AAT AAG GAT GCA GTG AAT CAC TTC CTC GAG CTA TAC AAA TTC GGA         351
Ser Asn Lys Asp Ala Val Asn His Phe Leu Glu Leu Tyr Lys Phe Gly
     75                  80                  85

TTC CTT CCA AGA GGT GCA ATC TAC TCC CTC TAT TAT CCT AAA CTC TTG         399
Phe Leu Pro Arg Gly Ala Ile Tyr Ser Leu Tyr Tyr Pro Lys Leu Leu
 90                  95                 100                     105

GAC GAG ACT AAA GCC TTG TTC AAA TTG TTC TAC TAT GCC AAG GAC TTT         447
Asp Glu Thr Lys Ala Leu Phe Lys Leu Phe Tyr Tyr Ala Lys Asp Phe
                110                 115                 120

GAT ACT TTC TAT AAA ACT GCC CTT TGG GCG AGA AAT CGT TTG AAC GAA         495
Asp Thr Phe Tyr Lys Thr Ala Leu Trp Ala Arg Asn Arg Leu Asn Glu
            125                 130                 135

GGT GAA TTC ATA TGT GCC TTC TAT GAA GCT GTC ATC CGG CGT CCC GAC         543
Gly Glu Phe Ile Cys Ala Phe Tyr Glu Ala Val Ile Arg Arg Pro Asp
            140                 145                 150

ACA GAG TAT CTC CAG TTA CCA CCG CCT TAT GAG TTA TAT CCC TAT GCG         591
Thr Glu Tyr Leu Gln Leu Pro Pro Tyr Glu Leu Tyr Pro Tyr Ala
        155                 160                 165

TTC TTC AAC AGT GAG GTA ATC GAG GCT GCA AAA AAT GCC AAA TTG TAC         639
Phe Phe Asn Ser Glu Val Ile Glu Ala Ala Lys Asn Ala Lys Leu Tyr
170                     175                 180                     185

AAT AAG CTT GTT GAA GGA AAT TCC TAC ATT ATC TAT GTC AAT TAC TCC         687
Asn Lys Leu Val Glu Gly Asn Ser Tyr Ile Ile Tyr Val Asn Tyr Ser
                190                 195                 200

GGC TGG TAC TTG AAT CGA GCT TAT GAT ACA GAG ATG AGA GTC AAC TAT         735
Gly Trp Tyr Leu Asn Arg Ala Tyr Asp Thr Glu Met Arg Val Asn Tyr
            205                 210                 215

TTC CTC GAA GAT ATC GGT TTA AAC ACC TTC TAC TTT TTC TAC CGC ATG         783
Phe Leu Glu Asp Ile Gly Leu Asn Thr Phe Tyr Phe Phe Tyr Arg Met
            220                 225                 230

GAT AAT CCA TTT TGG TTG AGC AGT GAG GAA TTT GGT TTG CAG AAA AAT         831
Asp Asn Pro Phe Trp Leu Ser Ser Glu Glu Phe Gly Leu Gln Lys Asn
        235                 240                 245

TTG CGT GGT GAG GAA TTT CTC TAT GTT CAC AAA ACA CTC TTG AAT CGT         879
Leu Arg Gly Glu Glu Phe Leu Tyr Val His Lys Thr Leu Leu Asn Arg
250                     255                 260                     265
```

TABLE 2-continued

BRH-I (SEQ. ID. NOS. 4 & 5)

| | | | | | | | | | | | | | | | | |
|---|---|---|---|---|---|---|---|---|---|---|---|---|---|---|---|---|
| TAC | AAT | TTG | GAA | AGA | TTG | GCA | AAT | GGC | TTG | GAG | AAA | ATT | GAA | GAA | TTC | 927 |
| Tyr | Asn | Leu | Glu | Arg 270 | Leu | Ala | Asn | Gly | Leu 275 | Glu | Lys | Ile | Glu | Glu 280 | Phe | |
| CTT | TGG | GAG | GGA | GAA | TTT | TAT | CCA | GGC | TAT | TAT | CCA | ACT | ATG | GTC | TAT | 975 |
| Leu | Trp | Glu | Gly 285 | Glu | Phe | Tyr | Pro | Gly 290 | Tyr | Tyr | Pro | Thr | Met 295 | Val | Tyr | |
| GGC | AAT | GGG | CTG | GCT | TAT | CCT | CAG | CGT | CCA | GGA | ATG | AGT | AGG | ATT | CCT | 1023 |
| Gly | Asn | Gly 300 | Leu | Ala | Tyr | Pro | Gln 305 | Arg | Pro | Gly | Met | Ser 310 | Arg | Ile | Pro | |
| CCA | TAT | AAG | TAT | CAT | TAT | TTA | CGG | TAT | ATC | CAC | GAT | ATC | GAA | GAT | AGA | 1071 |
| Pro | Tyr 315 | Lys | Tyr | His | Tyr | Leu 320 | Arg | Tyr | Ile | His | Asp 325 | Ile | Glu | Asp | Arg | |
| ATT | TCA | ACA | GCC | ATT | GAC | TTG | GGC | TAT | ATA | ATC | GAC | AGC | GAT | GGT | AGT | 1119 |
| Ile 330 | Ser | Thr | Ala | Ile | Asp 335 | Leu | Gly | Tyr | Ile | Ile 340 | Asp | Ser | Asp | Gly | Ser 345 | |
| CAC | CAC | AAC | ATC | TCA | AGT | CCC | GAA | GGA | CTT | AAC | CTC | TTA | GGT | AAC | ATC | 1167 |
| His | His | Asn | Ile | Ser 350 | Ser | Pro | Glu | Gly | Leu 355 | Asn | Leu | Leu | Gly | Asn 360 | Ile | |
| ATC | GAG | GGT | AAT | GAA | GAT | AGT | TGC | AAT | AAA | AAC | TTT | TAT | CAC | AGC | CTC | 1215 |
| Ile | Glu | Gly | Asn 365 | Glu | Asp | Ser | Cys | Asn 370 | Lys | Asn | Phe | Tyr | His 375 | Ser | Leu | |
| GAT | TGG | TAT | GGT | AGA | AAG | GTT | CTT | GGT | TTC | AAT | CTC | GAG | CCC | AAG | ACT | 1263 |
| Asp | Trp | Tyr 380 | Gly | Arg | Lys | Val | Leu 385 | Gly | Phe | Asn | Leu | Glu 390 | Pro | Lys | Thr | |
| CCC | TAT | CAA | GTT | ATT | CCA | AGT | GCA | CTA | GAG | TCA | TTT | TCA | ACT | TGC | ATG | 1311 |
| Pro | Tyr 395 | Gln | Val | Ile | Pro | Ser 400 | Ala | Leu | Glu | Ser | Phe 405 | Ser | Thr | Cys | Met | |
| AGA | GAT | CCG | GCT | TTC | TAT | CGT | CTC | TAC | AAT | AGA | TAT | CTG | TCA | TAC | TGG | 1359 |
| Arg | Asp | Pro | Ala | Phe 415 | Tyr | Arg | Leu | Tyr | Asn | Arg 420 | Tyr | Leu | Ser | Tyr | Trp 425 | |
| | | | | | | | | | | | | | | | | |
| Arg 410 | | | | | | | | | | | | | | | | |
| TAC | AGA | TTC | AAA | GAA | ACC | TTG | AAG | CCA | TAT | TCT | AAG | AAT | GAA | ATA | GTC | 1407 |
| Tyr | Arg | Phe | Lys | Glu 430 | Thr | Leu | Lys | Pro | Tyr 435 | Ser | Lys | Asn | Glu | Ile 440 | Val | |
| TTC | TCT | GAT | TTG | AAA | TTT | GAA | TCA | ATT | GCT | GTT | GAT | AAA | TTG | ATC | ACA | 1455 |
| Phe | Ser | Asp | Leu 445 | Lys | Phe | Glu | Ser | Ile 450 | Ala | Val | Asp | Lys | Leu 455 | Ile | Thr | |
| TAT | TTT | GAT | TAT | TTT | GAT | TCA | ACA | ATT | AGC | AAT | GGT | CTA | CCA | ATT | ACA | 1503 |
| Tyr | Phe | Asp 460 | Tyr | Phe | Asp | Ser | Thr 465 | Ile | Ser | Asn | Gly | Leu 470 | Pro | Ile | Thr | |
| AGT | AAA | CAA | GAT | GCT | GAT | AAT | TTA | ATG | ATC | AAA | GTT | CGC | CAG | AGT | CGT | 1551 |
| Ser | Lys 475 | Gln | Asp | Ala | Asp | Asn 480 | Leu | Met | Ile | Lys | Val 485 | Arg | Gln | Ser | Arg | |
| TTA | AAT | AAT | AAA | CAC | TTT | ACC | GTA | CAT | TTC | GCC | CTA | AAT | TCC | GAT | AAA | 1599 |
| Leu | Asn | Asn | Lys | His | Phe 495 | Thr | Val | His | Phe | Ala 500 | Leu | Asn | Ser | Asp | Lys 505 | |
| | | | | | | | | | | | | | | | | |
| 490 | | | | | | | | | | | | | | | | |
| GCA | CAA | AAA | GTT | GCC | ATT | CAG | CTG | TTT | CTT | GGA | CCC | AAA | TAT | GAT | GCA | 1647 |
| Ala | Gln | Lys | Val | Ala 510 | Ile | Gln | Leu | Phe | Leu 515 | Gly | Pro | Lys | Tyr | Asp 520 | Ala | |
| CTT | GGT | AAT | TTA | TTG | GAC | TTT | TCC | GAG | AGT | TAC | AAA | GAC | TTT | TAT | GAG | 1695 |
| Leu | Gly | Asn | Leu 525 | Leu | Asp | Phe | Ser | Glu 530 | Ser | Tyr | Lys | Asp | Phe 535 | Tyr | Glu | |
| ATT | GAC | TAC | TGG | ATT | ACT | GAT | GTG | AAT | GCT | GGC | TTG | AAT | AAA | CTT | GAA | 1743 |
| Ile | Asp | Tyr 540 | Trp | Ile | Thr | Asp | Val 545 | Asn | Ala | Gly | Leu | Asn 550 | Lys | Leu | Glu | |
| CGT | ACC | AGT | CAC | GAC | TTT | ATC | TTT | TTG | ATG | GCC | GAC | CGA | GAT | GAT | CCA | AGT | 1791 |
| Arg | Thr | Ser 555 | His | Asp | Phe | Ile | Phe 560 | Leu | Met | Ala | Asp | Arg 565 | Asp | Asp | Pro | Ser |

TABLE 2-continued

BRH-I (SEQ. ID. NOS. 4 & 5)

| GAA | ATT | TTA | TAC | AAA | AGA | GTT | TTA | AAG | GCC | CTT | GAT | GGA | AGT | GAA | AAG | 1839 |
| Glu | Ile | Leu | Tyr | Lys | Arg | Val | Leu | Lys | Ala | Leu | Asp | Gly | Ser | Glu | Lys | |
| 570 | | | | | 575 | | | | | 580 | | | | | 585 | |
| TTC | ATG | TAC | AAA | AAG | AAT | TTG | TAT | GGC | ATT | CCG | GAA | CGT | TTA | CTT | CTA | 1887 |
| Phe | Met | Tyr | Lys | Lys | Asn | Leu | Tyr | Gly | Ile | Pro | Glu | Arg | Leu | Leu | Leu | |
| | | | | 590 | | | | | 595 | | | | | 600 | | |
| CCA | AAA | GGT | AAA | CGT | GCC | GGT | AGT | ATT | TTC | CAA | CTG | TTT | GCC | TAT | GTA | 1935 |
| Pro | Lys | Gly | Lys | Arg | Ala | Gly | Ser | Ile | Phe | Gln | Leu | Phe | Ala | Tyr | Val | |
| | | | 605 | | | | | 610 | | | | | 615 | | | |
| AGC | CCA | GTT | ACC | CAG | CCA | GTC | ACC | TAC | AAA | TCA | CGA | GTA | TTT | GGA | TCT | 1983 |
| Ser | Pro | Val | Thr | Gln | Pro | Val | Thr | Tyr | Lys | Ser | Arg | Val | Phe | Gly | Ser | |
| | | 620 | | | | | 625 | | | | | 630 | | | | |
| TAT | CAA | TAC | TAC | ATG | AAA | CCA | GGT | GGT | TTT | CCA | CTG | GAC | AGG | CCA | ATC | 2031 |
| Tyr | Gln | Tyr | Tyr | Met | Lys | Pro | Gly | Gly | Phe | Pro | Leu | Asp | Arg | Pro | Ile | |
| | 635 | | | | | 640 | | | | | 645 | | | | | |
| TAC | TAT | CCC | CAT | TTC | CAA | GGG | CCC | AAT | ATG | TTC | TTC | AAA | GAT | ATT | ACG | |
| Tyr | Tyr | Pro | His | Phe | Gln | Gly | Pro | Asn | Met | Phe | Phe | Lys | Asp | Ile | Thr | |
| 650 | | | | | 655 | | | | | 660 | | | | | 665 | |
| ATT | TAC | CAC | AAG | ACT | GAT | GTG | GAT | CCT | AAT | GCT | ACT | ACC | TAATTCCAAT | | | 2128 |
| Ile | Tyr | His | Lys | Thr | Asp | Val | Asp | Pro | Asn | Ala | Thr | Thr | | | | |
| | | | | 670 | | | | | 675 | | | | | | | |

TTTTTTACTC TATTTTCATT TGAGATTCTT ATCAAATTCA ATGTTTGTTT GTTAATATTG 2188

TCTTTGTAGA GCTTAGAATG TTAGATTGAA AATGTTTATT TCCATGACAA TTTATTATTT 2248

GTTATTGATA TTATCAATGA ATTCTCTGTC AGTCAACCTC AGAGAATATA AAATTTTATT 2308

ACAAAAATGT CGTATTGAGC ATAAATTCAT TATTTGGGAA AAATTTTCAA ATAAAAAGCA 2368

TATTTTCCAA CAAAAAAAA 2387

What is claimed is:

1. A polypeptide designated Brh-1 isolated from the wasp *Bracon hebetor* which exhibits insect toxicity and has a molecular weight greater than 70 kDa and has the sequence of SEQ ID No. 5.

2. A polypeptide according to claim 1 wherein said polypeptide exhibits toxicity to insects of the order Lepidoptera.

3. A polypeptide according to claim 1 wherein said polypeptide exhibits toxicity to insects of the genus Spodoptera.

4. A method of controlling insects comprising exposing the insects to an insect controlling amount of the polypeptide according to claim 1.

5. An isolated polypeptide having the amino acid sequence of SEQ ID No. 5 which exhibits insect toxicity.

6. A method of controlling insects comprising exposing the insects to an insect controlling amount of the polypeptide according to claim 5.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 45 amino acids
        ( B ) TYPE: amino acid
        ( C ) STRANDEDNESS: single
        ( D ) TOPOLOGY: linear ( x i ) SEQUENCE DESCRIPTION: SEQ ID NO:1:

Xaa Thr Asp Phe Tyr Tyr Thr Asp Val Ile Ala Asp Gln Asp Phe Leu
        1               5                   10                  15

Leu Lys Gln Lys Lys Val Phe Gln Leu Leu Tyr His Val Ser Gln Pro
                        20                  25                  30

Xaa Ile Ser Asn Xaa Xaa Xaa Phe Gln Xaa Xaa Leu Lys
                    35                  40                  45

( 2 ) INFORMATION FOR SEQ ID NO:2:

( i ) SEQUENCE CHARACTERISTICS:
        ( A ) LENGTH: 28 amino acids (B) TYPE: amino acid
(C) STRANDEDNESS: single
(D) TOPOLOGY: linear (xi) SEQUENCE DESCRIPTION: SEQ ID NO:2:

```
Xaa His Val Gln Thr Tyr Thr Ala Asp Met Asp Phe Lys His Lys Gln
1               5                   10                  15

Lys Lys Ile Tyr His Leu Phe Xaa Xaa Xaa Xaa Gln
            20                  25
```

(2) INFORMATION FOR SEQ ID NO:3:

(i) SEQUENCE CHARACTERISTICS:
    (A) LENGTH: 41 amino acids
    (B) TYPE: amino acid
    (C) STRANDEDNESS: single
    (D) TOPOLOGY: linear (xi) SEQUENCE DESCRIPTION: SEQ ID NO:3:

```
Xaa Leu Phe Asp Phe Ile Val His Ala Lys Asp Ile Leu Gly Gly Ile
1               5                   10                  15

Asp Asn Leu Ala Lys Gly Ile Xaa Xaa Ala Ile Asn Lys Val Xaa Xaa
            20                  25                  30

Val Ile Xaa Lys Val Gln Xaa Gln Ala
            35                  40
```

(2) INFORMATION FOR SEQ ID NO:4:

(i) SEQUENCE CHARACTERISTICS:
    (A) LENGTH: 2387 base pairs
    (B) TYPE: nucleic acid
    (C) STRANDEDNESS: double
    (D) TOPOLOGY: linear (ix) FEATURE:
    (A) NAME/KEY: CDS
    (B) LOCATION: 85..2118
    (D) OTHER INFORMATION: /codon_start=85
        / number=1

(ix) FEATURE:
    (A) NAME/KEY: CDS
    (B) LOCATION: 85..2118
    (D) OTHER INFORMATION: /codon_start=85

(ix) FEATURE:
    (A) NAME/KEY: CDS
    (B) LOCATION: 85..2118

(xi) SEQUENCE DESCRIPTION: SEQ ID NO:4:

```
GCAACACAAG TGTTACTTCG TTTGCCACTT CACTGTTGAA GAAAAATAAA AAATACATTT      60

TGATTATCAC TTGAATAATC TATA ATG CTG AAG AAG GTC TTT CTT TTG GCC       111
                          Met Leu Lys Lys Val Phe Leu Leu Ala
                           1               5

TCT TTG GCT ATT ATC GTG ATA AAA GCT GAT ACC GAT TTT TAT TAT ACA      159
Ser Leu Ala Ile Ile Val Ile Lys Ala Asp Thr Asp Phe Tyr Tyr Thr
 10              15                  20                  25

GAT GTG ATA GCT GAT CAA GAT TTC CTT TTA AAG CAA AAG AAA GTT TTT      207
Asp Val Ile Ala Asp Gln Asp Phe Leu Leu Lys Gln Lys Lys Val Phe
                 30                  35                  40

CAA TTG TTG TAT CAT GTT TCA CAA CCA GAC ATC TCA AAT CCC GAG CTT      255
Gln Leu Leu Tyr His Val Ser Gln Pro Asp Ile Ser Asn Pro Glu Leu
             45                  50                  55

TTC CAG GAG GGA TTG GCT TAT GAC ATT GGA GCC AAT ATT GAT TCC TAT      303
Phe Gln Glu Gly Leu Ala Tyr Asp Ile Gly Ala Asn Ile Asp Ser Tyr
         60                  65                  70
```

| | | | | | | | | | | | | | | | | |
|---|---|---|---|---|---|---|---|---|---|---|---|---|---|---|---|---|
| TCT | AAT | AAG | GAT | GCA | GTG | AAT | CAC | TTC | CTC | GAG | CTA | TAC | AAA | TTC | GGA | 351 |
| Ser | Asn | Lys | Asp | Ala | Val | Asn | His | Phe | Leu | Glu | Leu | Tyr | Lys | Phe | Gly | |
| | 75 | | | | | 80 | | | | | 85 | | | | | |
| TTC | CTT | CCA | AGA | GGT | GCA | ATC | TAC | TCC | CTC | TAT | TAT | CCT | AAA | CTC | TTG | 399 |
| Phe | Leu | Pro | Arg | Gly | Ala | Ile | Tyr | Ser | Leu | Tyr | Tyr | Pro | Lys | Leu | Leu | |
| 90 | | | | 95 | | | | | 100 | | | | | 105 | | |
| GAC | GAG | ACT | AAA | GCC | TTG | TTC | AAA | TTG | TTC | TAC | TAT | GCC | AAG | GAC | TTT | 447 |
| Asp | Glu | Thr | Lys | Ala | Leu | Phe | Lys | Leu | Phe | Tyr | Tyr | Ala | Lys | Asp | Phe | |
| | | | | 110 | | | | | 115 | | | | | 120 | | |
| GAT | ACT | TTC | TAT | AAA | ACT | GCC | CTT | TGG | GCG | AGA | AAT | CGT | TTG | AAC | GAA | 495 |
| Asp | Thr | Phe | Tyr | Lys | Thr | Ala | Leu | Trp | Ala | Arg | Asn | Arg | Leu | Asn | Glu | |
| | | | 125 | | | | | 130 | | | | | 135 | | | |
| GGT | GAA | TTC | ATA | TGT | GCC | TTC | TAT | GAA | GCT | GTC | ATC | CGG | CGT | CCC | GAC | 543 |
| Gly | Glu | Phe | Ile | Cys | Ala | Phe | Tyr | Glu | Ala | Val | Ile | Arg | Arg | Pro | Asp | |
| | | 140 | | | | | 145 | | | | | 150 | | | | |
| ACA | GAG | TAT | CTC | CAG | TTA | CCA | CCG | CCT | TAT | GAG | TTA | TAT | CCC | TAT | GCG | 591 |
| Thr | Glu | Tyr | Leu | Gln | Leu | Pro | Pro | Pro | Tyr | Glu | Leu | Tyr | Pro | Tyr | Ala | |
| | 155 | | | | | 160 | | | | | 165 | | | | | |
| TTC | TTC | AAC | AGT | GAG | GTA | ATC | GAG | GCT | GCA | AAA | AAT | GCC | AAA | TTG | TAC | 639 |
| Phe | Phe | Asn | Ser | Glu | Val | Ile | Glu | Ala | Ala | Lys | Asn | Ala | Lys | Leu | Tyr | |
| 170 | | | | | 175 | | | | | 180 | | | | | 185 | |
| AAT | AAG | CTT | GTT | GAA | GGA | AAT | TCC | TAC | ATT | ATC | TAT | GTC | AAT | TAC | TCC | 687 |
| Asn | Lys | Leu | Val | Glu | Gly | Asn | Ser | Tyr | Ile | Ile | Tyr | Val | Asn | Tyr | Ser | |
| | | | | 190 | | | | | 195 | | | | | 200 | | |
| GGC | TGG | TAC | TTG | AAT | CGA | GCT | TAT | GAT | ACA | GAG | ATG | AGA | GTC | AAC | TAT | 735 |
| Gly | Trp | Tyr | Leu | Asn | Arg | Ala | Tyr | Asp | Thr | Glu | Met | Arg | Val | Asn | Tyr | |
| | | | 205 | | | | | 210 | | | | | 215 | | | |
| TTC | CTC | GAA | GAT | ATC | GGT | TTA | AAC | ACC | TTC | TAC | TTT | TTC | TAC | CGC | ATG | 783 |
| Phe | Leu | Glu | Asp | Ile | Gly | Leu | Asn | Thr | Phe | Tyr | Phe | Phe | Tyr | Arg | Met | |
| | | 220 | | | | | 225 | | | | | 230 | | | | |
| GAT | AAT | CCA | TTT | TGG | TTG | AGC | AGT | GAG | GAA | TTT | GGT | TTG | CAG | AAA | AAT | 831 |
| Asp | Asn | Pro | Phe | Trp | Leu | Ser | Ser | Glu | Glu | Phe | Gly | Leu | Gln | Lys | Asn | |
| | 235 | | | | | 240 | | | | | 245 | | | | | |
| TTG | CGT | GGT | GAG | GAA | TTT | CTC | TAT | GTT | CAC | AAA | ACA | CTC | TTG | AAT | CGT | 879 |
| Leu | Arg | Gly | Glu | Glu | Phe | Leu | Tyr | Val | His | Lys | Thr | Leu | Leu | Asn | Arg | |
| 250 | | | | | 255 | | | | | 260 | | | | | 265 | |
| TAC | AAT | TTG | GAA | AGA | TTG | GCA | AAT | GGC | TTG | GAG | AAA | ATT | GAA | GAA | TTC | 927 |
| Tyr | Asn | Leu | Glu | Arg | Leu | Ala | Asn | Gly | Leu | Glu | Lys | Ile | Glu | Glu | Phe | |
| | | | | 270 | | | | | 275 | | | | | 280 | | |
| CTT | TGG | GAG | GGA | GAA | TTT | TAT | CCA | GGC | TAT | TAT | CCA | ACT | ATG | GTC | TAT | 975 |
| Leu | Trp | Glu | Gly | Glu | Phe | Tyr | Pro | Gly | Tyr | Tyr | Pro | Thr | Met | Val | Tyr | |
| | | | 285 | | | | | 290 | | | | | 295 | | | |
| GGC | AAT | GGG | CTG | GCT | TAT | CCT | CAG | CGT | CCA | GGA | ATG | AGT | AGG | ATT | CCT | 1023 |
| Gly | Asn | Gly | Leu | Ala | Tyr | Pro | Gln | Arg | Pro | Gly | Met | Ser | Arg | Ile | Pro | |
| | | 300 | | | | | 305 | | | | | 310 | | | | |
| CCA | TAT | AAG | TAT | CAT | TAT | TTA | CGG | TAT | ATC | CAC | GAT | ATC | GAA | GAT | AGA | 1071 |
| Pro | Tyr | Lys | Tyr | His | Tyr | Leu | Arg | Tyr | Ile | His | Asp | Ile | Glu | Asp | Arg | |
| | 315 | | | | | 320 | | | | | 325 | | | | | |
| ATT | TCA | ACA | GCC | ATT | GAC | TTG | GGC | TAT | ATA | ATC | GAC | AGC | GAT | GGT | AGT | 1119 |
| Ile | Ser | Thr | Ala | Ile | Asp | Leu | Gly | Tyr | Ile | Ile | Asp | Ser | Asp | Gly | Ser | |
| 330 | | | | | 335 | | | | | 340 | | | | | 345 | |
| CAC | CAC | AAC | ATC | TCA | AGT | CCC | GAA | GGA | CTT | AAC | CTC | TTA | GGT | AAC | ATC | 1167 |
| His | His | Asn | Ile | Ser | Ser | Pro | Glu | Gly | Leu | Asn | Leu | Leu | Gly | Asn | Ile | |
| | | | | 350 | | | | | 355 | | | | | 360 | | |
| ATC | GAG | GGT | AAT | GAA | GAT | AGT | TGC | AAT | AAA | AAC | TTT | TAT | CAC | AGC | CTC | 1215 |
| Ile | Glu | Gly | Asn | Glu | Asp | Ser | Cys | Asn | Lys | Asn | Phe | Tyr | His | Ser | Leu | |
| | | | 365 | | | | | 370 | | | | | 375 | | | |
| GAT | TGG | TAT | GGT | AGA | AAG | GTT | CTT | GGT | TTC | AAT | CTC | GAG | CCC | AAG | ACT | 1263 |
| Asp | Trp | Tyr | Gly | Arg | Lys | Val | Leu | Gly | Phe | Asn | Leu | Glu | Pro | Lys | Thr | |
| | | 380 | | | | | 385 | | | | | 390 | | | | |

| | | | | | | | | | | | | | | | | |
|---|---|---|---|---|---|---|---|---|---|---|---|---|---|---|---|---|
| CCC | TAT | CAA | GTT | ATT | CCA | AGT | GCA | CTA | GAG | TCA | TTT | TCA | ACT | TGC | ATG | 1311 |
| Pro | Tyr 395 | Gln | Val | Ile | Pro | Ser 400 | Ala | Leu | Glu | Ser 405 | Phe | Ser | Thr | Cys | Met | |
| AGA | GAT | CCG | GCT | TTC | TAT | CGT | CTC | TAC | AAT | AGA | TAT | CTG | TCA | TAC | TGG | 1359 |
| Arg 410 | Asp | Pro | Ala | Phe 415 | Tyr | Arg | Leu | Tyr | Asn | Arg 420 | Tyr | Leu | Ser | Tyr | Trp 425 | |
| TAC | AGA | TTC | AAA | GAA | ACC | TTG | AAG | CCA | TAT | TCT | AAG | AAT | GAA | ATA | GTC | 1407 |
| Tyr | Arg | Phe | Lys | Glu 430 | Thr | Leu | Lys | Pro | Tyr 435 | Ser | Lys | Asn | Glu | Ile 440 | Val | |
| TTC | TCT | GAT | TTG | AAA | TTT | GAA | TCA | ATT | GCT | GTT | GAT | AAA | TTG | ATC | ACA | 1455 |
| Phe | Ser | Asp | Leu 445 | Lys | Phe | Glu | Ser | Ile 450 | Ala | Val | Asp | Lys | Leu 455 | Ile | Thr | |
| TAT | TTT | GAT | TAT | TTT | GAT | TCA | ACA | ATT | AGC | AAT | GGT | CTA | CCA | ATT | ACA | 1503 |
| Tyr | Phe | Asp 460 | Tyr | Phe | Asp | Ser | Thr 465 | Ile | Ser | Asn | Gly | Leu 470 | Pro | Ile | Thr | |
| AGT | AAA | CAA | GAT | GCT | GAT | AAT | TTA | ATG | ATC | AAA | GTT | CGC | CAG | AGT | CGT | 1551 |
| Ser | Lys 475 | Gln | Asp | Ala | Asp | Asn 480 | Leu | Met | Ile | Lys | Val 485 | Arg | Gln | Ser | Arg | |
| TTA | AAT | AAT | AAA | CAC | TTT | ACC | GTA | CAT | TTC | GCC | CTA | AAT | TCC | GAT | AAA | 1599 |
| Leu 490 | Asn | Asn | Lys | His | Phe 495 | Thr | Val | His | Phe | Ala 500 | Leu | Asn | Ser | Asp | Lys 505 | |
| GCA | CAA | AAA | GTT | GCC | ATT | CAG | CTG | TTT | CTT | GGA | CCC | AAA | TAT | GAT | GCA | 1647 |
| Ala | Gln | Lys | Val | Ala 510 | Ile | Gln | Leu | Phe | Leu 515 | Gly | Pro | Lys | Tyr | Asp 520 | Ala | |
| CTT | GGT | AAT | TTA | TTG | GAC | TTT | TCC | GAG | AGT | TAC | AAA | GAC | TTT | TAT | GAG | 1695 |
| Leu | Gly | Asn | Leu 525 | Leu | Asp | Phe | Ser | Glu 530 | Ser | Tyr | Lys | Asp | Phe 535 | Tyr | Glu | |
| ATT | GAC | TAC | TGG | ATT | ACT | GAT | GTG | AAT | GCT | GGC | TTG | AAT | AAA | CTT | GAA | 1743 |
| Ile | Asp | Tyr 540 | Trp | Ile | Thr | Asp | Val 545 | Asn | Ala | Gly | Leu | Asn 550 | Lys | Leu | Glu | |
| CGT | ACC | AGT | CAC | GAC | TTT | ATC | TTT | TTG | ATG | GCC | GAC | CGA | GAT | CCA | AGT | 1791 |
| Arg | Thr | Ser 555 | His | Asp | Phe | Ile | Phe 560 | Leu | Met | Ala | Asp | Arg 565 | Asp | Pro | Ser | |
| GAA | ATT | TTA | TAC | AAA | AGA | GTT | TTA | AAG | GCC | CTT | GAT | GGA | AGT | GAA | AAG | 1839 |
| Glu 570 | Ile | Leu | Tyr | Lys | Arg 575 | Val | Leu | Lys | Ala | Leu 580 | Asp | Gly | Ser | Glu | Lys 585 | |
| TTC | ATG | TAC | AAA | AAG | AAT | TTG | TAT | GGC | ATT | CCG | GAA | CGT | TTA | CTT | CTA | 1887 |
| Phe | Met | Tyr | Lys | Lys 590 | Asn | Leu | Tyr | Gly | Ile 595 | Pro | Glu | Arg | Leu | Leu 600 | Leu | |
| CCA | AAA | GGT | AAA | CGT | GCC | GGT | AGT | ATT | TTC | CAA | CTG | TTT | GCC | TAT | GTA | 1935 |
| Pro | Lys | Gly | Lys | Arg 605 | Ala | Gly | Ser | Ile | Phe 610 | Gln | Leu | Phe | Ala | Tyr 615 | Val | |
| AGC | CCA | GTT | ACC | CAG | CCA | GTC | ACC | TAC | AAA | TCA | CGA | GTA | TTT | GGA | TCT | 1983 |
| Ser | Pro | Val 620 | Thr | Gln | Pro | Val | Thr 625 | Tyr | Lys | Ser | Arg | Val 630 | Phe | Gly | Ser | |
| TAT | CAA | TAC | TAC | ATG | AAA | CCA | GGT | GGT | TTT | CCA | CTG | GAC | AGG | CCA | ATC | 2031 |
| Tyr | Gln | Tyr 635 | Tyr | Met | Lys | Pro | Gly 640 | Gly | Phe | Pro | Leu | Asp 645 | Arg | Pro | Ile | |
| TAC | TAT | CCC | CAT | TTC | CAA | GGG | CCC | AAT | ATG | TTC | TTC | AAA | GAT | ATT | ACG | 2079 |
| Tyr | Tyr | Pro 650 | His | Phe | Gln | Gly 655 | Pro | Asn | Met | Phe | Phe 660 | Lys | Asp | Ile | Thr 665 | |
| ATT | TAC | CAC | AAG | ACT | GAT | GTG | GAT | CCT | AAT | GCT | ACT | ACC | TAATTCCAAT | | | 2128 |
| Ile | Tyr | His | Lys | Thr 670 | Asp | Val | Asp | Pro | Asn 675 | Ala | Thr | Thr | | | | |

| | | | | |
|---|---|---|---|---|
| TTTTTTACTC | TATTTTCATT | TGAGATTCTT | ATCAAATTCA | ATGTTTGTTT | GTTAATATTG | 2188 |
| TCTTTGTAGA | GCTTAGAATG | TTAGATTGAA | AATGTTTATT | TCCATGACAA | TTTATTATTT | 2248 |
| GTTATTGATA | TTATCAATGA | ATTCTCTGTC | AGTCAACCTC | AGAGAATATA | AAATTTTATT | 2308 |
| ACAAAAATGT | CGTATTGAGC | ATAAATTCAT | TATTTGGGAA | AAATTTTCAA | ATAAAAAGCA | 2368 |

TATTTTCCAA CAAAAAAAA                                                                                  2387

(2) INFORMATION FOR SEQ ID NO:5:

(i) SEQUENCE CHARACTERISTICS:
        (A) LENGTH: 678 amino acids
        (B) TYPE: amino acid
        (D) TOPOLOGY: linear (ii) MOLECULE TYPE: protein (xi) SEQUENCE DESCRIPTION: SEQ ID NO:5:

```
Met Leu Lys Lys Val Phe Leu Leu Ala Ser Leu Ala Ile Ile Val Ile
 1               5                  10                  15

Lys Ala Asp Thr Asp Phe Tyr Tyr Thr Asp Val Ile Ala Asp Gln Asp
                20                  25                  30

Phe Leu Leu Lys Gln Lys Lys Val Phe Gln Leu Leu Tyr His Val Ser
            35                  40                  45

Gln Pro Asp Ile Ser Asn Pro Glu Leu Phe Gln Glu Gly Leu Ala Tyr
        50                  55                  60

Asp Ile Gly Ala Asn Ile Asp Ser Tyr Ser Asn Lys Asp Ala Val Asn
 65                  70                  75                  80

His Phe Leu Glu Leu Tyr Lys Phe Gly Phe Leu Pro Arg Gly Ala Ile
                85                  90                  95

Tyr Ser Leu Tyr Tyr Pro Lys Leu Leu Asp Glu Thr Lys Ala Leu Phe
                100                 105                 110

Lys Leu Phe Tyr Tyr Ala Lys Asp Phe Asp Thr Phe Tyr Lys Thr Ala
            115                 120                 125

Leu Trp Ala Arg Asn Arg Leu Asn Glu Gly Glu Phe Ile Cys Ala Phe
    130                 135                 140

Tyr Glu Ala Val Ile Arg Arg Pro Asp Thr Glu Tyr Leu Gln Leu Pro
145                 150                 155                 160

Pro Pro Tyr Glu Leu Tyr Pro Tyr Ala Phe Phe Asn Ser Glu Val Ile
                165                 170                 175

Glu Ala Ala Lys Asn Ala Lys Leu Tyr Asn Lys Leu Val Glu Gly Asn
            180                 185                 190

Ser Tyr Ile Ile Tyr Val Asn Tyr Ser Gly Trp Tyr Leu Asn Arg Ala
            195                 200                 205

Tyr Asp Thr Glu Met Arg Val Asn Tyr Phe Leu Glu Asp Ile Gly Leu
    210                 215                 220

Asn Thr Phe Tyr Phe Phe Tyr Arg Met Asp Asn Pro Phe Trp Leu Ser
225                 230                 235                 240

Ser Glu Glu Phe Gly Leu Gln Lys Asn Leu Arg Gly Glu Glu Phe Leu
                245                 250                 255

Tyr Val His Lys Thr Leu Leu Asn Arg Tyr Asn Leu Glu Arg Leu Ala
            260                 265                 270

Asn Gly Leu Glu Lys Ile Glu Glu Phe Leu Trp Glu Gly Glu Phe Tyr
            275                 280                 285

Pro Gly Tyr Tyr Pro Thr Met Val Tyr Gly Asn Gly Leu Ala Tyr Pro
    290                 295                 300

Gln Arg Pro Gly Met Ser Arg Ile Pro Pro Tyr Lys Tyr His Tyr Leu
305                 310                 315                 320

Arg Tyr Ile His Asp Ile Glu Asp Arg Ile Ser Thr Ala Ile Asp Leu
                325                 330                 335

Gly Tyr Ile Ile Asp Ser Asp Gly Ser His His Asn Ile Ser Ser Pro
            340                 345                 350
```

```
Glu  Gly  Leu  Asn  Leu  Leu  Gly  Asn  Ile  Ile  Glu  Gly  Asn  Glu  Asp  Ser
          355                      360                    365

Cys  Asn  Lys  Asn  Phe  Tyr  His  Ser  Leu  Asp  Trp  Tyr  Gly  Arg  Lys  Val
     370                      375                    380

Leu  Gly  Phe  Asn  Leu  Glu  Pro  Lys  Thr  Pro  Tyr  Gln  Val  Ile  Pro  Ser
385                      390                    395                         400

Ala  Leu  Glu  Ser  Phe  Ser  Thr  Cys  Met  Arg  Asp  Pro  Ala  Phe  Tyr  Arg
               405                    410                         415

Leu  Tyr  Asn  Arg  Tyr  Leu  Ser  Tyr  Trp  Tyr  Arg  Phe  Lys  Glu  Thr  Leu
               420                    425                    430

Lys  Pro  Tyr  Ser  Lys  Asn  Glu  Ile  Val  Phe  Ser  Asp  Leu  Lys  Phe  Glu
          435                    440                    445

Ser  Ile  Ala  Val  Asp  Lys  Leu  Ile  Thr  Tyr  Phe  Asp  Tyr  Phe  Asp  Ser
     450                    455                    460

Thr  Ile  Ser  Asn  Gly  Leu  Pro  Ile  Thr  Ser  Lys  Gln  Asp  Ala  Asp  Asn
465                      470                    475                         480

Leu  Met  Ile  Lys  Val  Arg  Gln  Ser  Arg  Leu  Asn  Asn  Lys  His  Phe  Thr
               485                    490                    495

Val  His  Phe  Ala  Leu  Asn  Ser  Asp  Lys  Ala  Gln  Lys  Val  Ala  Ile  Gln
               500                    505                    510

Leu  Phe  Leu  Gly  Pro  Lys  Tyr  Asp  Ala  Leu  Gly  Asn  Leu  Leu  Asp  Phe
          515                    520                    525

Ser  Glu  Ser  Tyr  Lys  Asp  Phe  Tyr  Glu  Ile  Asp  Tyr  Trp  Ile  Thr  Asp
     530                    535                    540

Val  Asn  Ala  Gly  Leu  Asn  Lys  Leu  Glu  Arg  Thr  Ser  His  Asp  Phe  Ile
545                      550                    555                         560

Phe  Leu  Met  Ala  Asp  Arg  Asp  Pro  Ser  Glu  Ile  Leu  Tyr  Lys  Arg  Val
               565                    570                    575

Leu  Lys  Ala  Leu  Asp  Gly  Ser  Glu  Lys  Phe  Met  Tyr  Lys  Lys  Asn  Leu
               580                    585                    590

Tyr  Gly  Ile  Pro  Glu  Arg  Leu  Leu  Leu  Pro  Lys  Gly  Lys  Arg  Ala  Gly
          595                    600                    605

Ser  Ile  Phe  Gln  Leu  Phe  Ala  Tyr  Val  Ser  Pro  Val  Thr  Gln  Pro  Val
     610                    615                    620

Thr  Tyr  Lys  Ser  Arg  Val  Phe  Gly  Ser  Tyr  Gln  Tyr  Tyr  Met  Lys  Pro
625                      630                    635                         640

Gly  Gly  Phe  Pro  Leu  Asp  Arg  Pro  Ile  Tyr  Tyr  Pro  His  Phe  Gln  Gly
               645                    650                    655

Pro  Asn  Met  Phe  Phe  Lys  Asp  Ile  Thr  Ile  Tyr  His  Lys  Thr  Asp  Val
               660                    665                    670

Asp  Pro  Asn  Ala  Thr  Thr
               675
```

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

ARYTGRAANA CYTTYTTYTG        20

( 2 ) INFORMATION FOR SEQ ID NO:7:

( i ) SEQUENCE CHARACTERISTICS:

(A) LENGTH: 20 base pairs
(B) TYPE: nucleic acid
(C) STRANDEDNESS: single
(D) TOPOLOGY: linear (xi) SEQUENCE DESCRIPTION: SEQ ID NO:7:

GAYTTYTAYT AYACNGAYGT                                                                              20

(2) INFORMATION FOR SEQ ID NO:8:

(i) SEQUENCE CHARACTERISTICS:
(A) LENGTH: 22 base pairs
(B) TYPE: nucleic acid
(C) STRANDEDNESS: single
(D) TOPOLOGY: linear (xi) SEQUENCE DESCRIPTION: SEQ ID NO:8:

GGAAATCTTG ATCAGCTATC AC                                                                           22

(2) INFORMATION FOR SEQ ID NO:9:

(i) SEQUENCE CHARACTERISTICS:
(A) LENGTH: 31 amino acids
(B) TYPE: amino acid
(C) STRANDEDNESS: single
(D) TOPOLOGY: linear (xi) SEQUENCE DESCRIPTION: SEQ ID NO:9:

Thr Asp Phe Tyr Tyr Thr Asp Val Ile Ala Asp Gln Asp Phe Leu Leu
 1               5                  10                  15

Lys Gln Lys Lys Val Phe Gln Leu Leu Tyr His Val Ser Gln Pro
            20                  25                  30

(2) INFORMATION FOR SEQ ID NO:10:

(i) SEQUENCE CHARACTERISTICS:
(A) LENGTH: 93 base pairs
(B) TYPE: nucleic acid
(C) STRANDEDNESS: single
(D) TOPOLOGY: linear (xi) SEQUENCE DESCRIPTION: SEQ ID NO:10:

ACNGAYTTYT AYTAYACNGA YGTNATHGCN GAYCARGAYT TYYTNYTNAA RCARAARAAR                                  60

GTNTTYCARY TNYTNTAYCA YGTNWSNCAR CCN                                                               93

(2) INFORMATION FOR SEQ ID NO:11:

(i) SEQUENCE CHARACTERISTICS:
(A) LENGTH: 68 base pairs
(B) TYPE: nucleic acid
(C) STRANDEDNESS: single
(D) TOPOLOGY: linear (xi) SEQUENCE DESCRIPTION: SEQ ID NO:11:

GATTTTTATT ATACTGATGT GATAGCTGAT CAAGATTTCC TTTTAAAGCA AAAGAAGGTT                                  60

TTTCAATT                                                                                          68

(2) INFORMATION FOR SEQ ID NO:12:

(i) SEQUENCE CHARACTERISTICS:
(A) LENGTH: 68 base pairs
(B) TYPE: nucleic acid
(C) STRANDEDNESS: single
(D) TOPOLOGY: linear (xi) SEQUENCE DESCRIPTION: SEQ ID NO:12:

GACTTTTATT ACACTGACGT GATAGCTGAT CAAGATTTCC TTTTAAAGCA AAAAAAGGTA     60

TTTCAACT     68

( 2 ) INFORMATION FOR SEQ ID NO:13:

( i ) SEQUENCE CHARACTERISTICS:
        ( A ) LENGTH: 68 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:13:

GATTTTTATT ATACTGATGT GATAGCTGAT CAAGATTTCC TTTTAAAGCA AAAGAAGGTA     60

TTTCAACT     68